(12) United States Patent
Botsford et al.

(10) Patent No.: US 11,147,467 B1
(45) Date of Patent: Oct. 19, 2021

(54) REAL TIME ELECTRONIC/DIAGNOSTIC DEVICE FOR COVID-19 AND OTHER DISEASES

(71) Applicant: Anapole Technologies Inc., Des Moines, IA (US)

(72) Inventors: Stephen F. Botsford, Barrington, IL (US); Vitaly M. Seltser, Zelenaya (RU); Joseph F. Startari, North Royalton, OH (US)

(73) Assignee: ANAPOLE TECHNOLOGIES INC., Des Moines, IA (US)

( * ) Notice: Subject to any disclaimer, the term of this patent is extended or adjusted under 35 U.S.C. 154(b) by 0 days.

(21) Appl. No.: 17/220,769

(22) Filed: Apr. 1, 2021

Related U.S. Application Data

(60) Provisional application No. 63/004,327, filed on Apr. 2, 2020.

(51) Int. Cl.
*A61B 5/055* (2006.01)
*A61N 2/00* (2006.01)
(Continued)

(52) U.S. Cl.
CPC .............. *A61B 5/055* (2013.01); *A61N 2/004* (2013.01); *G01R 1/025* (2013.01); *G01R 23/16* (2013.01); *G16H 50/00* (2018.01)

(58) Field of Classification Search
CPC ........ A61B 5/055; G01R 1/025; G01R 23/16; A61N 2/004; G16H 50/00
(Continued)

(56) References Cited

U.S. PATENT DOCUMENTS

| | | |
|---|---|---|
| 5,658,234 A | 8/1997 | Dunlavy |
| 6,503,191 B1 | 1/2003 | Miller |

(Continued)

OTHER PUBLICATIONS

Gallego, O., "Nonsurgical treatment of recurrent gliblastoma", Current Oncology, vol. 22, No. 4: e273-e281, Aug. 2015, Multimed Inc. www.current-oncology.com.
(Continued)

*Primary Examiner* — Giovanni Astacio-Oquendo
(74) *Attorney, Agent, or Firm* — Baker & McKenzie LLP

(57) ABSTRACT

An electromagnetic resonance-based disease detecting system may comprising a spectrum analyzer assembly comprised of one of a spectrum analyzer with an internal tracking generator or a spectrum analyzer with a separate signal generator, a radiating antenna electronically connected to the spectrum analyzer assembly output and configured to radiate a subject with an electromagnetic field based on a resonant frequency signal, wherein radiating a subject with the electromagnetic field generates a subject spectrum; a receiving antenna configured to receive the subject spectrum; a spectrum analyzer electronically connected to the receiving antenna and configured to receive the subject spectrum from the receiving antenna; and a processor, the processor being operatively connected to the spectrum analyzer assembly, the radiating antenna, the receiving antenna, and the spectrum analyzer, wherein the processor is configurable to store and control the resonant frequency signal generated by the spectrum analyzer assembly output control the electromagnetic field radiated from the radiating antenna; and, compare the received subject spectrum to the generated resonant frequency signal using the spectrum analyzer assembly input controlled by the processor to determine an absence or a presence of the disease condition without the use of chemical reagents or testing supplies.

20 Claims, 15 Drawing Sheets

(51) Int. Cl.
 *G16H 50/00* (2018.01)
 *G01R 1/02* (2006.01)
 *G01R 23/16* (2006.01)

(58) Field of Classification Search
 USPC .................... 324/200, 300, 301, 307, 309
 See application file for complete search history.

(56) References Cited

U.S. PATENT DOCUMENTS

| | | | |
|---|---|---|---|
| 9,610,458 B1* | 4/2017 | Botsford | A61N 2/02 |
| 10,279,190 B2 | 5/2019 | Botsford et al. | |
| 2008/0021526 A1 | 1/2008 | Kokorin | |
| 2008/0062068 A1 | 3/2008 | Kokorin | |
| 2008/0199851 A1* | 8/2008 | Egan | B01L 3/5029 |
| | | | 435/5 |
| 2014/0330268 A1 | 11/2014 | Palti et al. | |
| 2018/0001105 A1* | 1/2018 | Botsford | A61N 2/004 |
| 2018/0217073 A1* | 8/2018 | Chen | G01R 33/246 |
| 2019/0146047 A1* | 5/2019 | Weinberg | G01R 33/5608 |
| | | | 324/309 |
| 2020/0265328 A1* | 8/2020 | Kaditz | G06N 3/0472 |

OTHER PUBLICATIONS

Foletti, A. et al., "Bioelectromagnetic medicine: The role of resonance signaling", Electromagnetic Biology and Medicine, 2013; 32(4): 484-499, downloaded by University of Eastern Finland on Nov. 19, 2015, ISSN: 1536-8386 (Online) Journal homepage: http://www.tandfonline.com/loi/iebm20.

Liboff, A.R., "Electric-Field Ion Cyclotron Resonance", Bioelectromagnetics, 18:85-87 (1997).

* cited by examiner

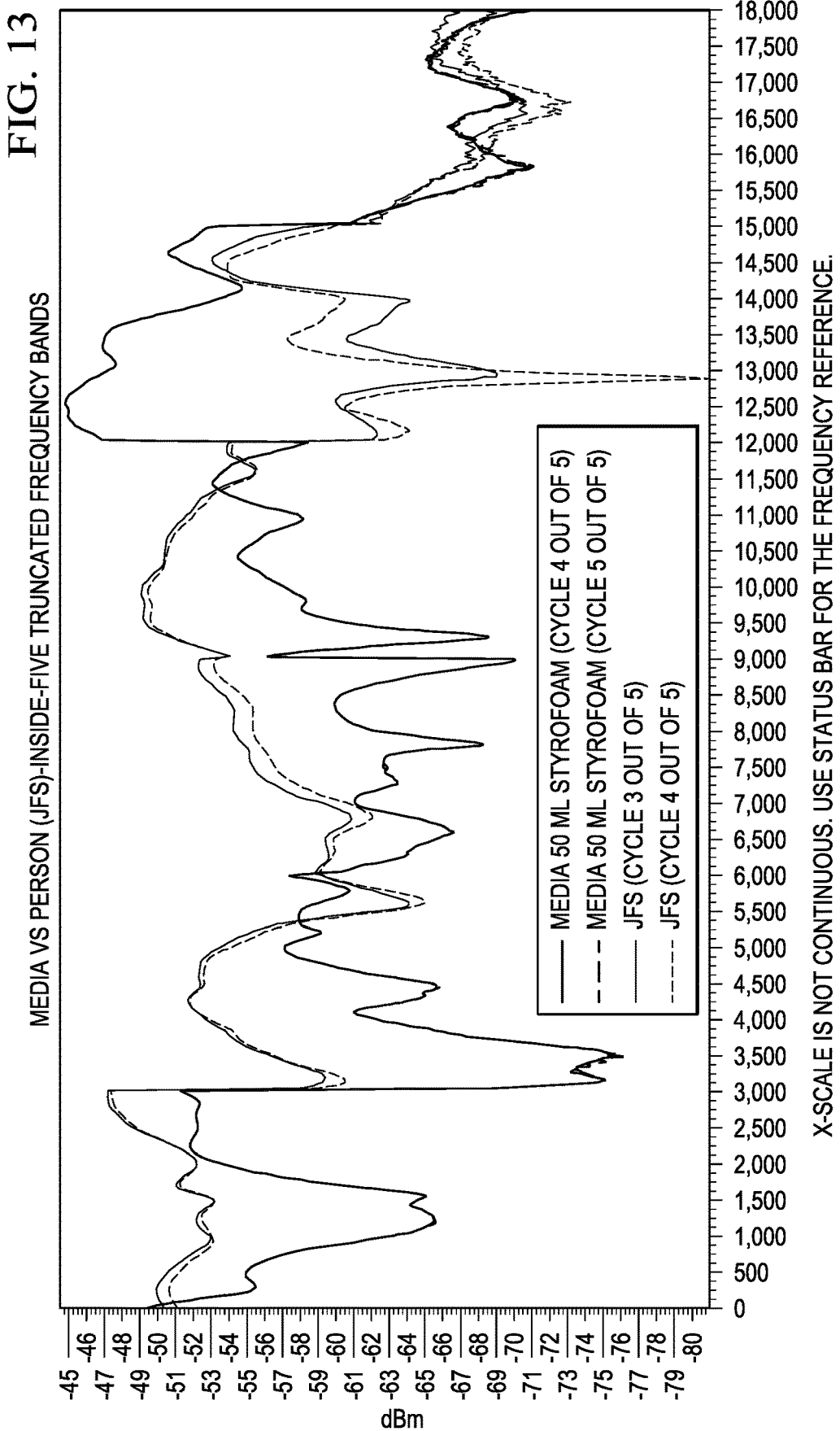

REAL TIME ELECTRONIC/DIAGNOSTIC DEVICE FOR COVID-19 AND OTHER DISEASES

CROSS-REFERENCE TO RELATED APPLICATION

This application claims priority to U.S. Provisional Application No. 63/004,327 filed Apr. 2, 2020, the content of which is hereby incorporated in its entirety by reference.

TECHNICAL FIELD

The present disclosure relates, in some embodiments, to detecting, diagnosing, and treating diseases such as the COVID-19 virus by using resonance-based electromagnetic radiation.

BACKGROUND

The global pandemic caused by the coronavirus COVID-19 has infected a million people and is projected to infect millions more. Expansive testing is required to determine areas of high concentration, isolate infected patients, prevent transmission, protect healthcare personnel, and truncate spread of the virus. Depending on the test method, diagnosis time may take hours or even days, and results cannot be entered into a comprehensive data base until they are received, thereby increasing administrative effort and costs. Further, this pandemic has created critical shortages in testing supplies (swabs, reagents, etc.) and in personal protective equipment (PPE) and is poised to negatively affect both public and private healthcare systems in the United States and around the globe. But current, assay based, testing methods rely on key chemical reagents/supplies as well as biological samples from a patient and therefore require direct person to person contact with the patient, exposing medical personnel and potentially the patient thus requiring a more extensive use of testing supplies and PPE. Medical personnel who conduct the tests have to use PPE, and any shortage in PPE puts at risk medical professionals who are fighting for patients at the frontline. Therefore, there is an urgent need for faster diagnostic technologies, as well as technologies that can help reduce the need for costly testing supplies and PPE.

SUMMARY

Accordingly, a need has arisen for an electromagnetic resonance-based disease detecting system including (a) a spectrum analyzer assembly comprising one of a spectrum analyzer with an internal tracking generator or a spectrum analyzer with a separate signal generator, which output is configured to generate a resonant frequency signal that carries at least one frequency at which reference materials relate to a disease condition resonate; (b) a radiating antenna electronically connected to the output of the spectrum analyzer assembly and configured to radiate a subject with an electromagnetic field based on the resonant frequency signal, wherein radiating a subject with the electromagnetic field generates a subject spectrum; (c) a receiving antenna configured to receive the subject spectrum; (d) a spectrum analyzer assembly the input of which is electronically connected to the receiving antenna and configured to receive the subject spectrum from the receiving antenna; and (d) a processor, the processor being operatively connected to the radiating antenna, the receiving antenna, and both the input and output of the spectrum analyzer assembly. A processor may be configurable to: (i) control a resonant frequency signal generated by the spectrum analyzer assembly (ii) control an electromagnetic field radiated from a radiating antenna; and (iii) control a spectrum analyzer to determine one of an absence and a presence of a disease condition resonate.

An electromagnetic resonance-based disease detecting system may include a patient testing station comprising a station comprising a frame or station that supports the radiating antenna, and a receiving antenna. A patient testing station may include a communication device containing one or more of a computer terminal, an audio communicator and a video communicator. An electromagnetic resonance-based disease detecting system may include a remote monitoring and check-in station comprising one or more computer terminals and one or more user interfaces, wherein the remote monitoring and check-in station may be in electronic communication with the patient testing station; a patient check-in station comprising one or more computer terminals and one or more user interfaces, wherein the patient check-in station may be in electronic communication with the remote monitoring and check-in station; and a patient check-in station comprising one or more computer terminals and one or more user interfaces, wherein the patient check-in station may be in electronic communication with the remote monitoring and check-in station.

An electromagnetic resonance-based disease detecting system may include a cart configured to support and transport a spectrum analyzer assembly, antenna supports, positive/negative test result lights, a radiating antenna, and a receiving antenna. A radiating antenna may be supported by a stand and includes a radiating antenna connector that may permit the radiating antenna to be stationed at a distance from about 1 foot to about 10 feet from a cart while maintaining an electronic connection with the spectrum analyzer assembly output, and a processor. A system processor may include an algorithm that activates automatic test result lights attached to the radiating and receiving antenna. A receiving antenna may be supported by a stand and includes a receiving antenna connector that permits the receiving antenna to be stationed at a distance from about 1 foot to about 5 feet from the cart while maintaining the electronic connection with the spectrum analyzer assembly input and the processor.

A disease condition resonate may include a coronavirus (or its specific oligonucleotides) selected from the group consisting of a severe respiratory syndrome coronavirus, a virus, an RNA virus, a SARS-CoV-2, a Middle East Respiratory syndrome-related coronavirus (MERS-CoV), a human coronavirus NL63 (HCoV-NL63), a human coronavirus HKU1 (HCoV-HKU1), a human coronavirus OC43 (HCoV-OC43), a human coronavirus 229E (HCoV-229E), and a combination thereof. A severe acute respiratory syndrome coronavirus may be a strain of COVID-19. An electromagnetic resonance-based disease detecting system may include a cart configured to support and transport a spectrum analyzer, a radiating antenna, and a receiving antenna, wherein the radiating antenna may include a radiating antenna connector that may permit the radiating antenna to be stationed at a distance from about 1 foot to about 10 feet or greater from the cart while maintaining an electronic connection with a signal generator and a processor. A receiving antenna may include a receiving antenna connector that permits the receiving antenna to be stationed at a distance from about 1 foot to about 10 feet or greater from the cart while maintaining the electronic connection with a spectrum analyzer and a processor. A station may be tall and wide enough to accommodate a standing patient. For example, the station may have a height ranging from 1 foot to 15 feet, a length ranging from 1 foot to 15 feet, and a width ranging from 1 foot to 15 feet.

An electromagnetic resonance-based disease detecting system may include a container defining a void for holding one or more of a housing, a spectrum analyzer assembly, the radiating antenna, the receiving antenna, and the processor within the container. A container may be configured to transport one or more of a housing, a radiating antenna, a receiving antenna, a spectrum analyzer assembly and a processor from a first location to a second location. A radiating antenna may include a radiating antenna connector that permits the radiating antenna to be stationed at a distance from 1 foot to 30 feet from the container to position it suitably on the patient while maintaining an electronic connection with the output of the spectrum analyzer assembly, and a processor. A receiving antenna may include a receiving antenna connector that permits the receiving antenna to be stationed at a distance from 1 foot to 30 feet from a container while maintaining an electronic connection with input of the spectrum analyzer assembly and a processor.

An electromagnetic resonance-based disease detecting system may include one or more rechargeable batteries may be configured for supplying power to a spectrum analyzer assembly, a radiating antenna, a receiving antenna and a processor. electronically connected to one or more of the, a radiating antenna, a spectrum analyzer assembly, a receiving antenna, and a processor. A container may include one or more straps that may be attached to a face of the container, wherein the one or more straps are configured to secure the container to an operator.

A method for detecting a disease may include exposing a patient to a testing system configured to radiate an electromagnetic field based on a frequency map, the frequency map comprising one or more resonant frequencies of the virus; and determining whether the patient carries the virus in a matter of seconds (e.g., 30 seconds or less) after exposing the patient to the testing system. A testing system may be a portable system such as a handheld device. A method may include applying a series of filters in a testing system to at least partially remove background radiation to facilitate detection of a virus in an open environment.

A method for detecting a virus may include isolating resonant frequencies of the virus (or its specific oligonucleotides) including a primary frequency and one or more harmonic frequencies in a shielded facility; refining accuracy of the isolated resonant frequencies using a spectrum analyzer; developing a frequency map based on the refined resonant frequencies; and radiating an electromagnetic field based on the frequency map for detecting the virus. A method may include an isolating of a resonant frequencies includes a live patient methodology, and an isolating of a resonant frequencies includes a specific target methodology. A virus includes a coronavirus (or its specific oligonucleotides) selected from the group consisting of a severe respiratory syndrome coronavirus, an RNA virus, a SARS-CoV-2, a Middle East Respiratory syndrome-related coronavirus (MERS-CoV), a human coronavirus NL63 (HCoV-NL63), a human coronavirus HKU1 (HCoV-HKU1), a human coronavirus OC43 (HCoV-OC43), a human coronavirus 229E (HCoV-229E), and a combination thereof. A method may include transmitting the frequency map electronically to a remote location. A method may include applying one or more filters to at least partially remove background radiation to facilitate detection of the virus in an open environment.

BRIEF DESCRIPTION OF THE DRAWINGS

Some of the embodiments of the disclosure may be understood by referring, in part, to the present disclosure and accompany drawings, where:

FIG. 13 illustrates a truncated spectra from cycles 4 and 5 of 50 ML of media in a Styrofoam container vs the truncated spectra from and cycles 3 and 4 of a person (JF Startari), according to a specific example embodiment of the disclosure.

DETAILED DESCRIPTION

Figure 1:
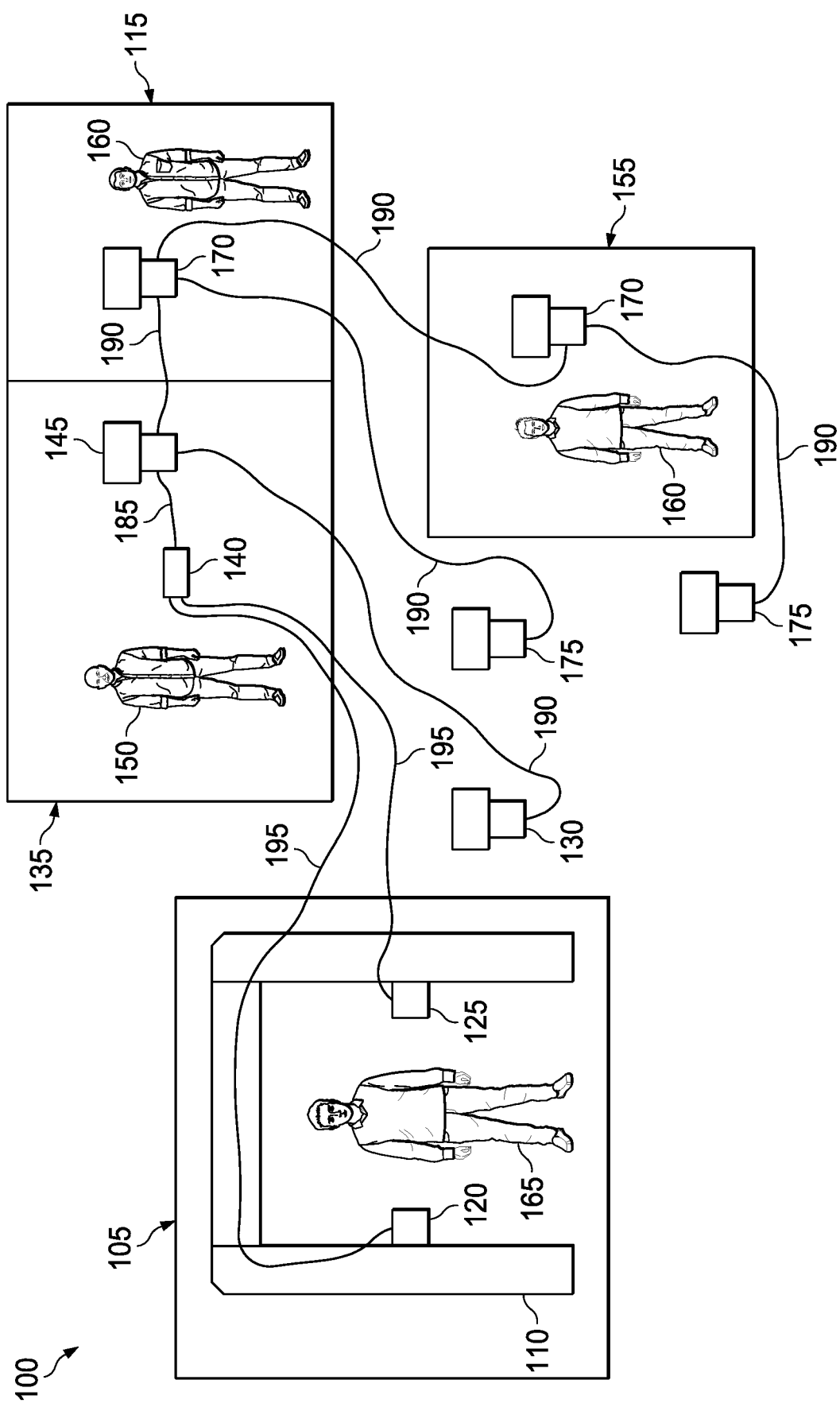
FIG. 1 illustrates a point of entry, remotely controlled, electronic, real time, diagnostic device for a disease, according to a specific example embodiment of the disclosure.

The present disclosure relates, in some embodiments, to systems and methods for rapidly detecting (e.g., in 30 seconds or less) the presence of diseases such as a coronavirus (e.g., COVID-19) in a patient by using resonance-based electromagnetic radiation. Further, in some embodiments, testing can be performed remotely, that is, without exposing medical personnel to the patient, which will help slow the spread of the virus.

A real time electronic diagnostic technology disclosed herein may detect the presence of one or more diseases (e.g., pathogens, cancer, and other abnormalities) or antibodies. Disclosed technology uses a device that generates an electromagnetic field to excite and detect resonant frequencies of the disease. It may be implemented as a (1) point of entry, remotely controlled, electronic, real time, diagnostic device, (2) a portable, point of care, electronic, real time, diagnostic device, (3) handheld, point of care, electronic, real time, diagnostic device, and/or (4) a portable, point of entry, automatic, electronic, real time, diagnostic device. The technology may instantaneously detect the presence of COVID-19 virus (or its antibodies) electronically, needs no reagents or other supplies; and, in some embodiments, without the need for personal protective equipment (PPE). The technology would bring various benefits such as significant reduction in testing time/testing supplies; screening at point of entry (POE) or point of care (POC) as well as among the general population; immediate isolation of infected patients; significantly less exposure of medical personnel; significant reduction in usage of PPE; quick identification of areas with a high concentration of infections; concurrent update of databases; and/or being waivable under the FDA's Clinical Laboratory Improvement Amendments (CLIA).

According to an embodiment, developing a diagnostic method may begin with selecting a particular disease to be targeted. A disease may include one or more of a severe respiratory syndrome coronavirus, a virus, an RNA virus, a Severe Acute Respiratory Syndrome Coronavirus (SARS-CoV), a Middle East Respiratory syndrome-related coronavirus (MERS-CoV), a human coronavirus NL63 (HCoV-NL63), a human coronavirus HKU1 (HCoV-HKU1), a human coronavirus OC43 (HCoV-OC43), a human coronavirus 229E (HCoV-229E), and SARS-CoV-2 (COVID-19). Next, a primary frequency (and harmonics) of the target disease may be isolated. Resonant frequencies for the target may be isolated based on live patient methodology or a specific target methodology. Isolation of a resonant frequency may be performed in a Faraday chamber, which may help eliminate background electromagnetic interference (EMI). In some embodiments, a system may be configured using properly configured components (e.g., antennas, test and measurement equipment, etc.) to measure various parameters such as an amplitude of resonance frequency (and harmonics). An accuracy of frequency determination may be refined using a spectrum analyzer assembly comprising one of a spectrum analyzer with an internal tracking generator or a spectrum analyzer with a separate signal generator and/or a network analyzer. Once a primary frequency and related harmonics are isolated, a frequency map may be developed for a particular disease and incorporated into a diagnosis software for field testing. Simultaneously, the software's existing database may be expanded to include patient data; test results, etc. In an embodiment, diagnostic device broadcasts may be limited to resonant frequencies instead of a broad frequency spectrum to detect a disease. During development of the disclosed technology, test accuracy using live patients and/or specifically targeted materials in a shielded facility may confirm efficacy of device. And once efficacy is proven in the shielded facility, it may be tested in an open environment, during which live field tests are conducted with patients and/or targeted materials. Portable point of care and point of entry devices may be deployed. With component miniaturization, a handheld, mobile device may be deployed for field use.

Point of Entry Disease Testing System

FIG. 1 illustrates disease testing system 100 according to an embodiment of the disclosure, where a disease may be tested, screened, detected, or diagnosed with targeted electromagnetic radiation. A disease testing system 100 may include a patient check-in station with audio/video communication/computer terminal 130, 175, a remote patient check-in station 115, 155, a remote patient check-in/monitoring station 135 and a patient testing station 105, which may be electronically connected to each other through wires or wirelessly. A patient 165 may be initially received, during times of heavy traffic at a patient check-in station audio/video communication/computer terminal 175, where they may input their identification information and communicate with a check-in specialist 160. During periods of low traffic, a patient 165 may be initially received, at a patient check-in station audio/video communication/computer terminal 130 to a disease testing system 100 operator 150. During operation of a disease testing system 100, a patient 165 may be 10 or more feet away from an operator 150 at all times so that no PPE is required. After using a patient check-in station audio/video communication/computer terminal 175, a patient may proceed to a patient testing station 105, where the patient 165 may be exposed to an electromagnetic field to determine an absence or a presence of a disease (e.g., COVID-19). Determination of a presence or an absence of a disease may take only a few seconds and the detection results are provided to an operator 150 stationed at a remote monitoring and check-in station 135. For example, determination of a presence or an absence of a disease using a disclosed system may take 30 seconds or less, or 25 seconds or less, or 20 seconds or less, or 15 seconds or less, or 10 seconds or less, or 5 seconds or less, or 1 second or less, where about incudes plus or minus 2.5 seconds. Determination of a presence or an absence of a disease using a disclosed system may take from 1 second to 5 seconds, or from 5 seconds to 10 seconds, or from 10 seconds to 15 seconds, or from 15 seconds to 20 seconds, or from 20 seconds to 25 seconds, or from 25 seconds to 30 seconds, where about includes plus or minus 2.5 seconds. An operator 150 may communicate with a patient 165 at all times through audio/video communication/computer terminal 130.

As shown in FIG. 1, a disease testing system 100 may include a patient testing station 105. A patient testing station 105 may include an antenna support frame 110 A patient testing station 105 may be any general size, as long as transmission strength and antenna separation are matched, so that one or more patients 165 may enter the testing station 105 and be tested for one or more diseases (e.g., COVID-19). Patient testing station 105 may be set up in the open, under a shelter or inside a building. For example, a testing station 105 may have antenna spacing of 3 feet and a frame height of 8 feet to accommodate a single person. Group patient testing requires farther separation and multiple antennas; For example, an antenna support used for group analysis may have receiving antennas spaced 4 feet apart and transmitting antennas in parallel to the receiving antennas spaced 6 feet apart. While group testing is possible; its application with this device may be less efficient than individual testing since once a positive result is found for the group, each patient must be retested individually. An antenna support frame 110 may be tall and wide enough to accommodate a standing patient. For example, antenna support frame 110 may have a height of about 1 foot, or about 2 feet, or about 3 feet, or about 4 feet, or about 5 feet, or about 6 feet, or about 7 feet, or about 8 feet, or about 9 feet, or about 10 feet, or about 11 feet, or about 12 feet, or about 13 feet, or about 14 feet, or about 15 feet, or more, where about includes plus or minus 0.5 feet. An antenna support frame 110 may have a width of about 1 foot, or of about 2 feet, or about 4 feet, or about 5 feet, or about 6 feet, or about 7 feet, or about 8 feet, or about 9 feet, or about 10 feet, or about 11 feet, or about 12 feet, or about 13 feet, or about 14 feet, or about 15 feet, or more, where about includes plus or minus 0.5 feet. An antenna support frame 110 may have a length ranging from about 1 foot to about 15 feet. In an embodiment, antenna support frame 110 has a height, length, and width, each ranging from about 1 foot to about 10 feet. For example, an antenna support frame 110 may have any number of walls having a length of about 1 foot, or about 2 feet, or about 3 feet, or about 4 feet, or about 5 feet, or about 6 feet, or about 7 feet, or about 8 feet, or about 9 feet, or about 10 feet, or about 11 feet, or about 12 feet, or about 13 feet, or about 14 feet, or about 15 feet, or more, where about includes plus or minus 0.5 feet.

A patient testing station 105 may include one or more audio/video communication/computer terminals 130, which may provide for a visual and/or auditory communication between a patient 165 and an operator 150 that is at least 10 feet away from the patient 165. A communicator 130 may be connected to a computer 145 contained in a remote monitoring and check-in station 135 through a testing station communicator connector 190 or through wireless connection means including WIFI, Bluetooth, Zigbee, NFC, WIMAX, UMTS, LTE, and others. A patient testing station 105 may include one or more radiating antennae 120 and one or more receiving antennae 125. A radiating antenna 120 may be configured to radiate a patient 165 with an electromagnetic field based on a resonant frequency signal generated by a spectrum analyzer with tracking generator or a spectrum analyzer with separate signal generator controlled by a computer 145 operated by an operator 150.

In some embodiments, a resonant frequency may be selected and extracted from a reference material rather than capturing one from an ever present, stabilized reference source. This allows a diagnostic application to be conducted without need for a reference material after the resonant frequency has been digitized and stored electronically in a system 100 computer 145. A spectrum analyzer assembly 140 may be connected to a radiating antennae 120 and a receiving antenna 125 through antenna connectors 195. A receiving antenna 125 may be configured to receive an electromagnetic spectrum signal that has been reflected, refracted, and/or transmitted off of or through a patient 165. A spectrum analyzer assembly 140 may also be connected to a radiating antenna 120 and a receiving antenna 125 through an antenna connector 195.

As is shown in FIG. 1, a disease testing system 100 may include a remote monitoring and check-in station 135 that includes one or more computer terminals 145. A remote monitoring and check-in station 135 may include a booth, a table, a chair, a mobile station, a computer terminal, and a combination thereof. A computer terminal 145 may include a user interface with controlling software, a patient database, audio communication equipment, and visual communication equipment. A computer terminal 145 may be electronically connected to a spectrum analyzer with tracking generator (or separate signal generator) through direct physical connection of General Purpose Interface Bus (or similar connector) 185. A computer terminal 145 may be electronically connected to each of a patient check-in audio/video communication/computer terminal 130 and a patient testing station 105 through direct physical connection of one or more wires 190 or wirelessly (e.g., WIFI, Bluetooth, etc.). A remote monitoring and check-in station 135 may provide an operator 150 with a place to monitor a disease state of a patient 165 while not requiring PPE due to achieving a safe minimum proximity between the operator 150 and the patient 165. For example, a remote monitoring and check-in station 135 may be any distance away from a patient testing station 105, Having such a spacing between a monitoring station 135 and a patient testing station 105 may prevent direct contact between an operator 150 and a patient 165.

Disease testing system 100 may be deployed indoors or outdoors. For example, patients 165 can drive up to the patient check-in terminal 175, give their information to the check-in specialist 160 who will login the information on computer 170; or patient may directly log into terminal 175. In an indoor deployment, for example, check-in can be accomplished at the check-in terminals (175, 130), followed by the testing station situated in a hallway or a designated room. Patient 165 information can be entered into a common database, and patients 165 can be directed to walk on a controlled basis to the patient testing station 105 (e.g., if outdoors, patients can park their car and then proceed). In an embodiment, a minimum distance (e.g., 10 feet, 12 feet, etc.) separates the patient check-in terminal/audio/visual communicators (130, 175), the patients 165 to be tested, and the patient testing station 105 in order to minimize airborne transmission of the disease.

Patients 165 are then tested at the patient testing station 105 using technologies disclosed herein. After being instructed, via communicators 130, to enter the patient testing station 105 (e.g., similar to millimeter wave screening process in airports), a patient 165 is exposed to the electromagnetic field briefly (e.g., a matter of seconds) for testing. The patient 165 may be instructed to remain still for the short duration of the testing. Then the patient 165 waits until the system registers a positive or negative result. This result may be automatically updated in a test database. If a disease (e.g., COVID-19) is diagnosed in a patient 165, that patient 165 may be notified of the result and directed to go back to their vehicle, go home and isolate; or proceed to the COVID-19 section of the hospital or medical center for admittance. If the presence of a disease is not found, the patient 165 may be given the result, released to go home, enter the premises or go to work. Continuous decontamination of the patient test station 105 may be done through application of high intensity UV light, a disinfectant spray (e.g., ethanol solution), or both.

Portable Point of Care Real Time Disease Testing System

Figure 2:
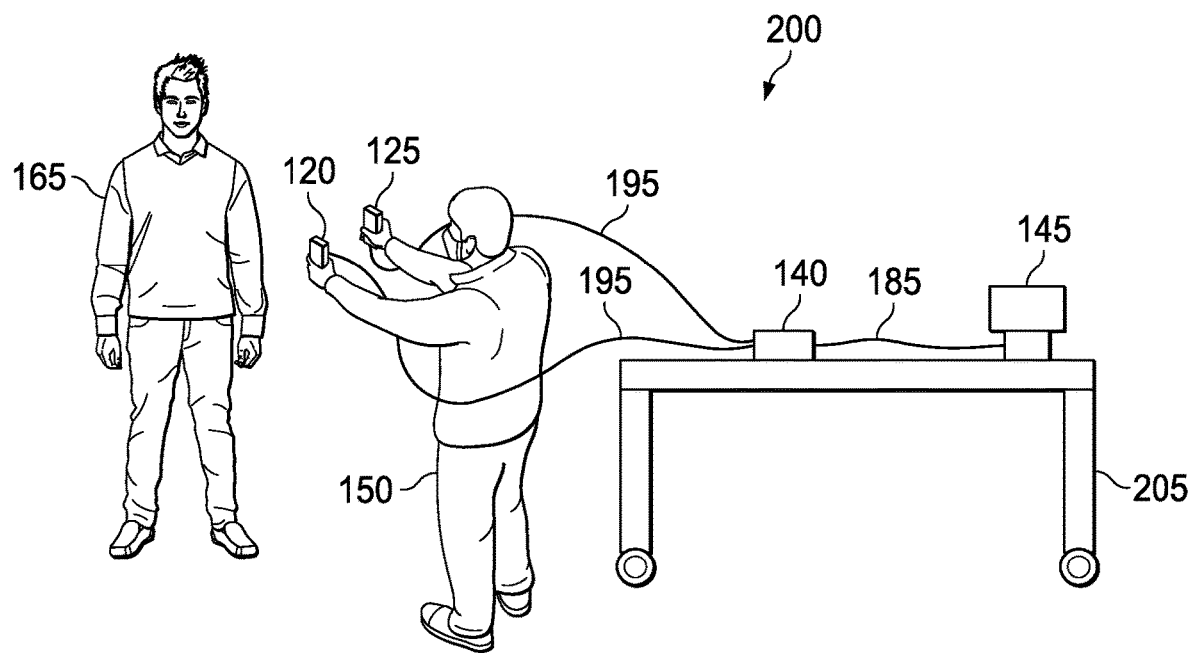
FIG. 2 illustrates a portable, point of care electronic, real time, diagnostic device for a disease, according to a specific example embodiment of the disclosure.

As is shown in FIG. 2, the present disclosure relates to a portable point of care disease testing system 200. A portable point of care disease testing system 200 may be used to test, screen, detect, and diagnose a disease in a patient 165 using targeted electromagnetic radiation. As shown in FIG. 2, a portable disease testing system 200 includes a cart 205 configured to support and transport a radiating antenna 120, a receiving antenna 125, a spectrum analyzer assembly which includes one of a spectrum analyzer with an internal tracking generator or a spectrum analyzer with separate signal generator comprise device 140, which is controlled by a computer 145 A portable point of care disease testing system 200 may include one or more rechargeable batteries (charged via photovoltaic means or a 120 volt electrical source) electronically connected to a computer, a radiating antenna, a receiving antenna, a spectrum analyzer with tracking generator (or separate signal generator), and a processor; or may run on normal 120 volt power. The working systems of system 100 and 200 are similar in principle, except for system 200 may be readily transported from a first location to a second location by an operator 150. For example, portable disease testing system 200 may be transported from a first location to a second location that is in workable proximity to a patient 165. Components of a portable disease testing system 200 may be temporarily removed from a cart 205 while remaining electronically connected to other components remaining on the cart. For example, an operator 150 may remove a radiating antenna 120 and a receiving antenna 125 from a cart 205 while a computer 145 and a spectrum analyzer assembly 140 remain on the cart 200 to properly accommodate a patient in prone position. In this configuration, an operator 150 may detect a presence or an absence of a disease (e.g., COVID-19) on a patient 165 without having to operate a permanent or semi-permanent testing system. In some embodiments, an operator 150 may use hand-held antenna (120, 125) or may position the antenna (120, 125) in a location relative to a patient 165 being tested.

Hand Held Real Time Disease Testing System

Figure 3:
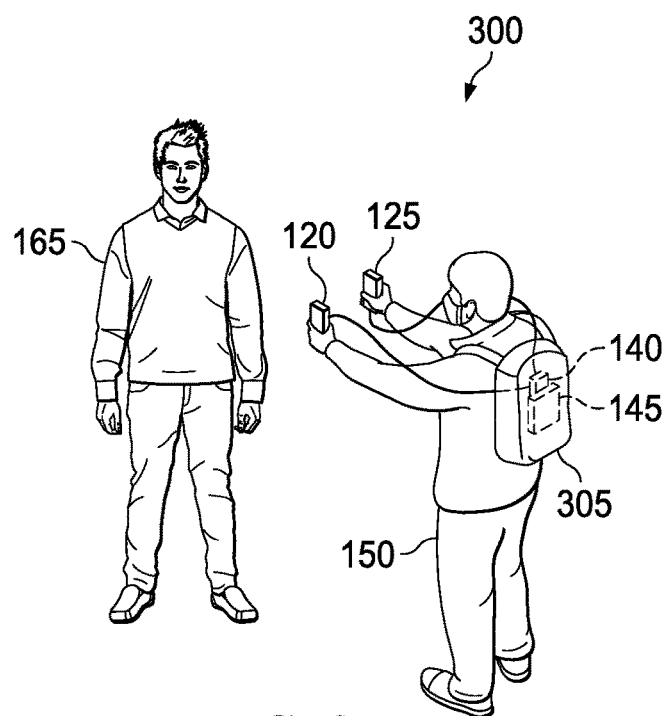
FIG. 3 illustrates a hand held, point of care, electronic, real time diagnostic device for detecting a disease, according to a specific example embodiment of the disclosure.

FIG. 3 illustrates a mobile, portable disease testing system 300 according to an embodiment of the disclosure. Similar to disease testing system 200, disease testing system 300 is a portable system carried by an operator 150 (e.g., handheld or in a backpack) to conduct the testing on a patient 165. In both systems 200 and 300, PPE such as protective gown and face mask may be recommended since the patient and care giver may be in close proximity. As shown in FIG. 3, a mobile, portable disease testing system 300 may include a container 305 configured to support and transport a radiating antenna 120, a receiving antenna 125, a spectrum analyzer assembly which includes one of a spectrum analyzer with an internal tracking generator or a spectrum analyzer with separate signal generator 140, controlled by a computer 145. A mobile, portable disease testing system 300 may include one or more rechargeable batteries (either charged via photovoltaic means or a 120 volt electrical source) electronically connected to a spectrum analyzer assembly, a radiating antenna, a receiving antenna, and a processor. One or more components of a portable disease testing system 300 may be temporarily removed from a container 305 so that a patient 165 may be tested for a disease (e.g., COVID-19) or treated for a disease (e.g., COVID-19). For example, an operator 150 may remove a radiating antenna 120 and a receiving antenna 125 from a container 305 while a computer 145 controlling a spectrum analyzer assembly which includes one of a spectrum analyzer with an internal tracking generator or a spectrum analyzer with separate signal generator 140 remain in the container 305. In this configuration, an operator 150 may detect a presence or an absence of a disease (e.g., COVID-19) on a patient 165 without having to operate a permanent or semi-permanent testing system. In some embodiments, an operator 150 may use hand-held antenna (120, 125) or may position the antenna (120, 125) in a location relative to a patient 165 being tested.

Point of Entry, Portable Automated, Real Time Disease Testing System

Figure 4:
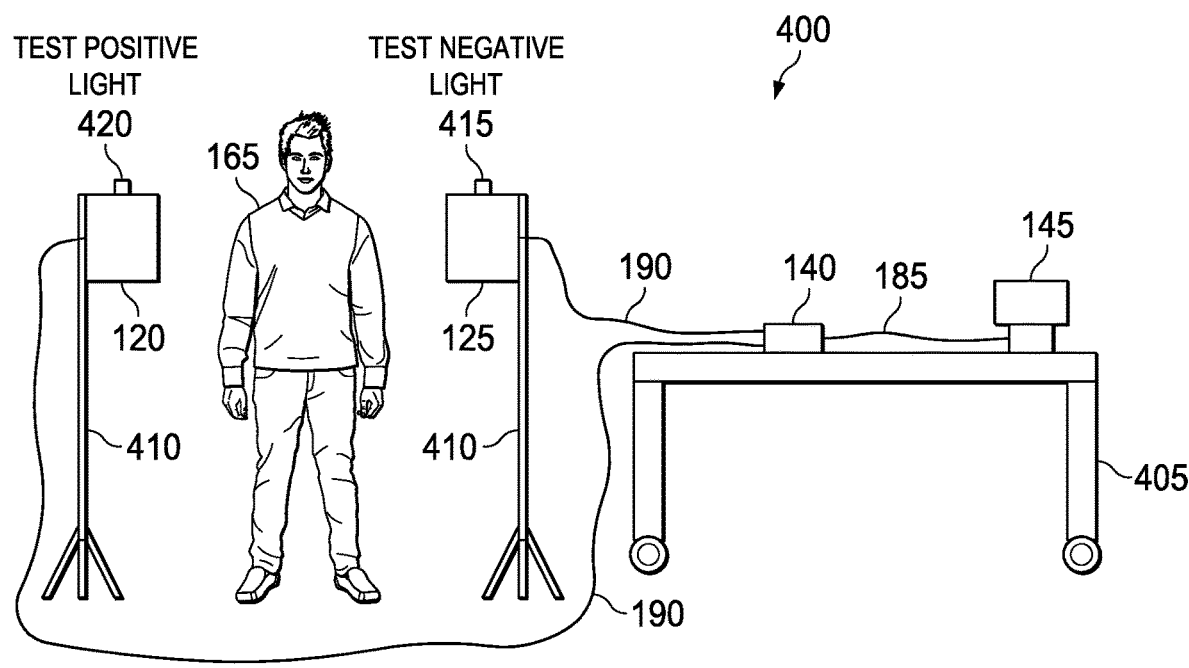
FIG. 4 illustrates a portable, point of entry, automated, electronic, real time, diagnostic device for a disease, according to a specific example embodiment of the disclosure.

FIG. 4 illustrates an automated portable disease testing system 400 according to an embodiment of the disclosure. As with other disease testing systems herein, no testing reagents or supplies may be required. Similar to disease testing system 200, disease testing system 400 is a portable system put in place by an operator 150 to conduct the testing on a person 165. Unlike both systems 200 and 300, PPE such as protective gown and face mask may not be required since the person and operator may not be in close proximity. As shown in FIG. 4, a portable disease testing system 400 may be configured to support and transport a radiating antenna 120, a receiving antenna 125, antenna support stands 410, a spectrum analyzer assembly which includes one of a spectrum analyzer with an internal tracking generator and a spectrum analyzer with separate signal generator 140, controlled by a computer 145 using cart 205. An automated portable disease testing system 400 may include one or more rechargeable batteries (charged either via photovoltaic means or a 120 volt electrical source) electronically connected to a signal generator, a radiating antenna, a receiving antenna, a spectrum analyzer, and a processor; or may be operated on standard 120 volt power. In this automated configuration, system 400 may detect a presence or an absence of a disease (e.g., COVID-19) on a person 165 without an operator 150 in close proximity. In some embodiments, card swipe capability may automatically record a particular person's 165 disease status.

In some embodiments, when a spectrum analyzer assembly which includes one of a spectrum analyzer with an internal tracking generator or a spectrum analyzer with separate signal generator is used 140 and controlled by a computer 145, with appropriate software, of a system (100, 200, 300, 400) disclosed herein. A spectrum analyzer assembly output may be capable of generating thousands of pulses (points) over a selected bandwidth. A spectrum analyzer assembly output may be synchronized (synced) to the spectrum analyzer assembly input by each frequency pulse, and as a result, a digital fingerprint (spectra) of a particular reference material may be mapped and included in a software (SPAN 32) database that may be contained with a computer 145 of any system disclosed here.

A disclosed system 100 may operate using a bandwidth of 6 GHz, which may continually broadcast a digital signal. Such operation may have an advantage over known systems that required a 3.5 GHz bandwidth while using a sweep function (not continuous as disclosed herein), where resonant pulses can only be identified by using a signal generator in a peak hold function where resonant frequencies are not illuminated continuously due to a timing of when the pulses irradiate at a particular frequency. In some embodiments, a full span spectra of each reference material may be mapped and compared with others to determine areas of significant spectral difference. For example, spectrum of a single scan of an empty vial may be subtracted from both a spectral scan of a media filled vial and a second scan of an empty vial. This may better highlight distinct spectral variations of different substances; where the optimum frequency bands are noted. Once identified, portions of each frequency band with greatest difference between the substances are manually selected (truncated) and entered into a frequency map database. This truncated spectral fingerprint may now be used to detect a presence of a particular substance (e.g., disease) in a much shorter period of time than when using a full bandwidth spectral fingerprint. Such an analysis can be done in seconds rather than minutes. Although scan time is associated with the speed of the particular equipment and the bandwidth, standard off the shelf spectrum analyzers/signal generators may be used effectively with this system/software. As an example, assume sweep time for a span of 1 kHz is 10 μs; and, the total bandwidth of truncated frequency bands is 500 MHz (i.e. 50 MHz, 225, MHz, 100 MHz, 25 MHz); total scan time for each cycle will be 5 seconds (total frequency band in hertz divided by the span swept in hertz times the sweep time per span equals cycle time or 500,000,000 [500 MHz]÷1,000,000 [1 kHz]×10 [number of micro seconds]÷1,000,000,000 [number micro seconds per second]=5 seconds [time per cycle]. Since such a truncated spectral fingerprint may be digitized, it may also be used to diagnose or treat a disease more effectively and efficiently. Prior existing technology requires a number of lengthy scans to ensure that resonant frequencies were activated sufficiently (analog modulation missed frequencies periodically since bandwidth was swept) and could not accurately identify which frequency was associated with a reference material and which frequencies are associated with stabilization materials. In addition, the broadband characteristics of the prior existing technology necessitated full bandwidth scanning as compared with the present technology's truncated bandwidth capability. The prior existing technology could not perform detection or diagnostic in real time (e.g., less than 15 minutes) due to the need for full bandwidth scans.

Once extraction/digitization of a spectral fingerprint (truncated or full bandwidth) has been accomplished, the resulting frequency maps may be stored in a database. Individual frequency maps and/or the full database may be transmitted to any device worldwide instantaneously via streaming, email or other electronic means, which may provide a fast response to address a mutating or new disease. In some embodiments, spectral mapping may be performed while operating inside a Faraday chamber, which may enhance both specificity and sensitivity when detecting minute quantities of a target material in comparison to similar operations being performed without the Faraday chamber.

As shown in FIG. 4, the simple configuration of system 400 (e.g., without the need for a patient database) allows it to be deployed in various flexible and portable settings. For example, system 400 may be deployed in a sporting event, school, or educational setting, where people pass through the test station upon arrival at the facility/premises. A green light 415 may indicate a negative COVID-19 test (in which case the person proceeds), while a red light 420 may indicate a positive COVID-19 test (in which case the person may be asked to leave). For example, in the case of employers, card swipes may be used. For healthcare providers, patients may log themselves in.

Disease Detection and Treatment System

Figure 5A:
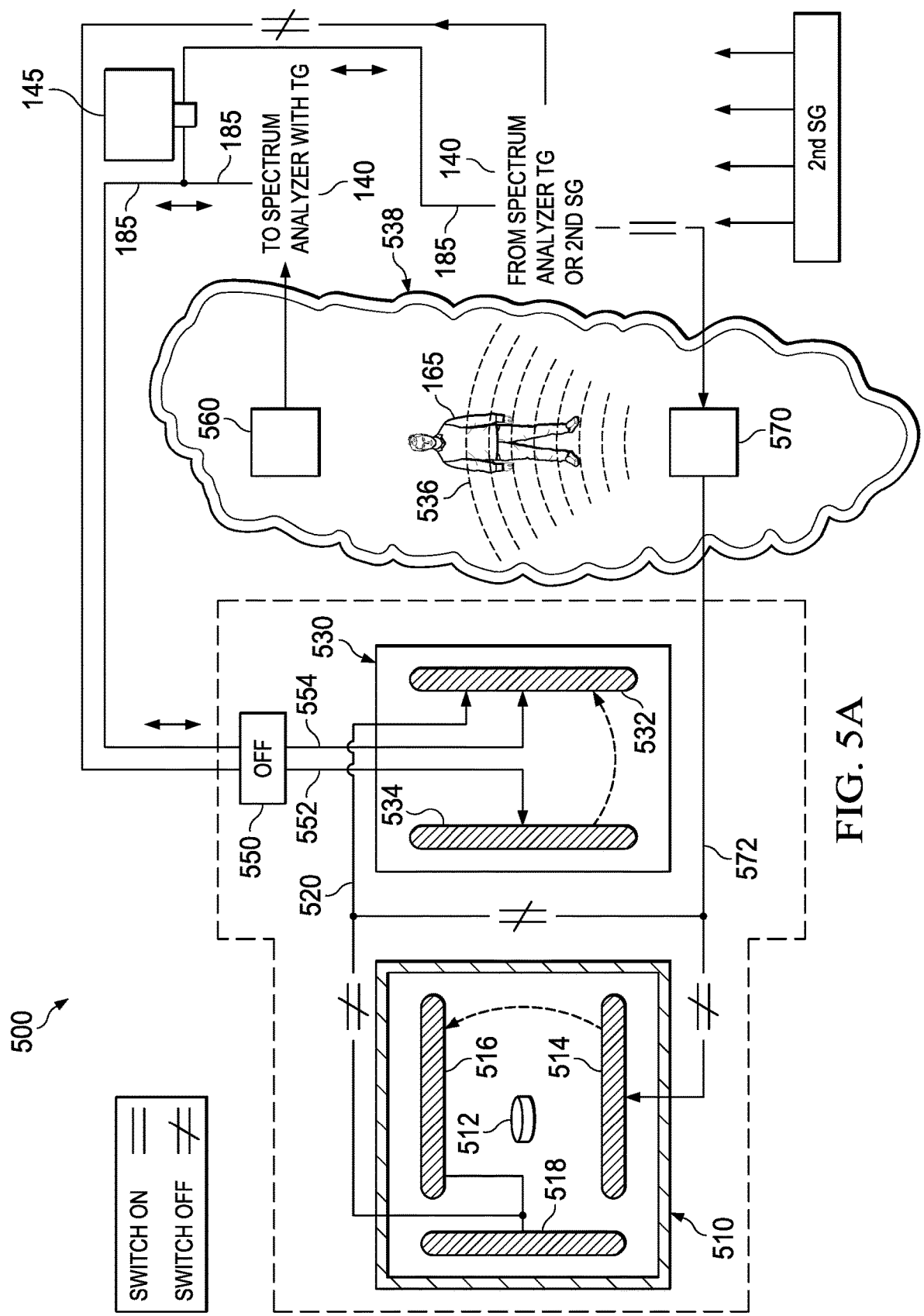
FIG. 5A illustrates a disease detection system in a diagnostic configuration that may transmit a resonant frequency without a reference material according to a specific example embodiment of the disclosure.
Figure 5B:
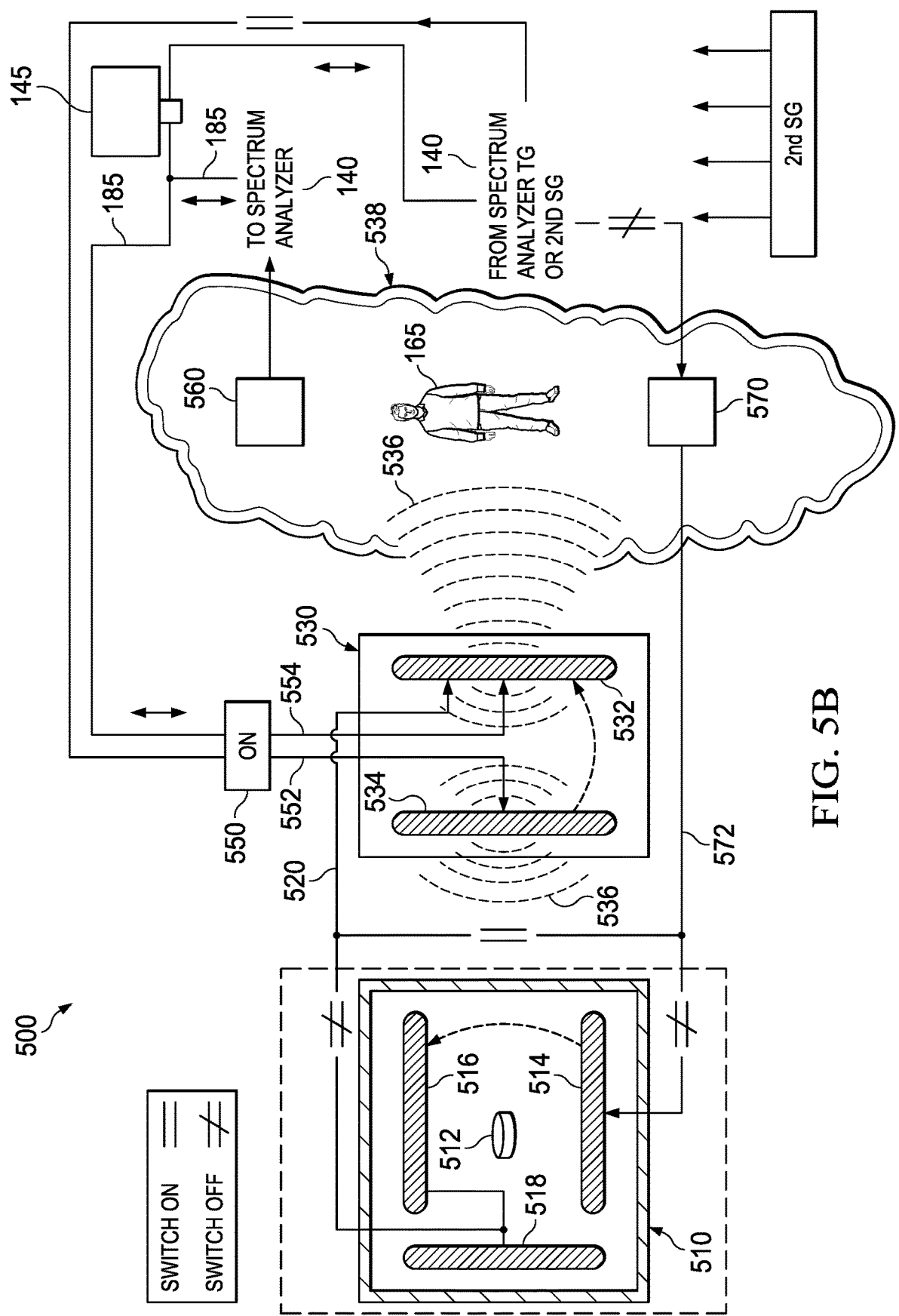
FIG. 5B illustrates a disease detection system in a treatment configuration using electronic frequency maps, according to a specific example embodiment of the disclosure.
Figure 5C:
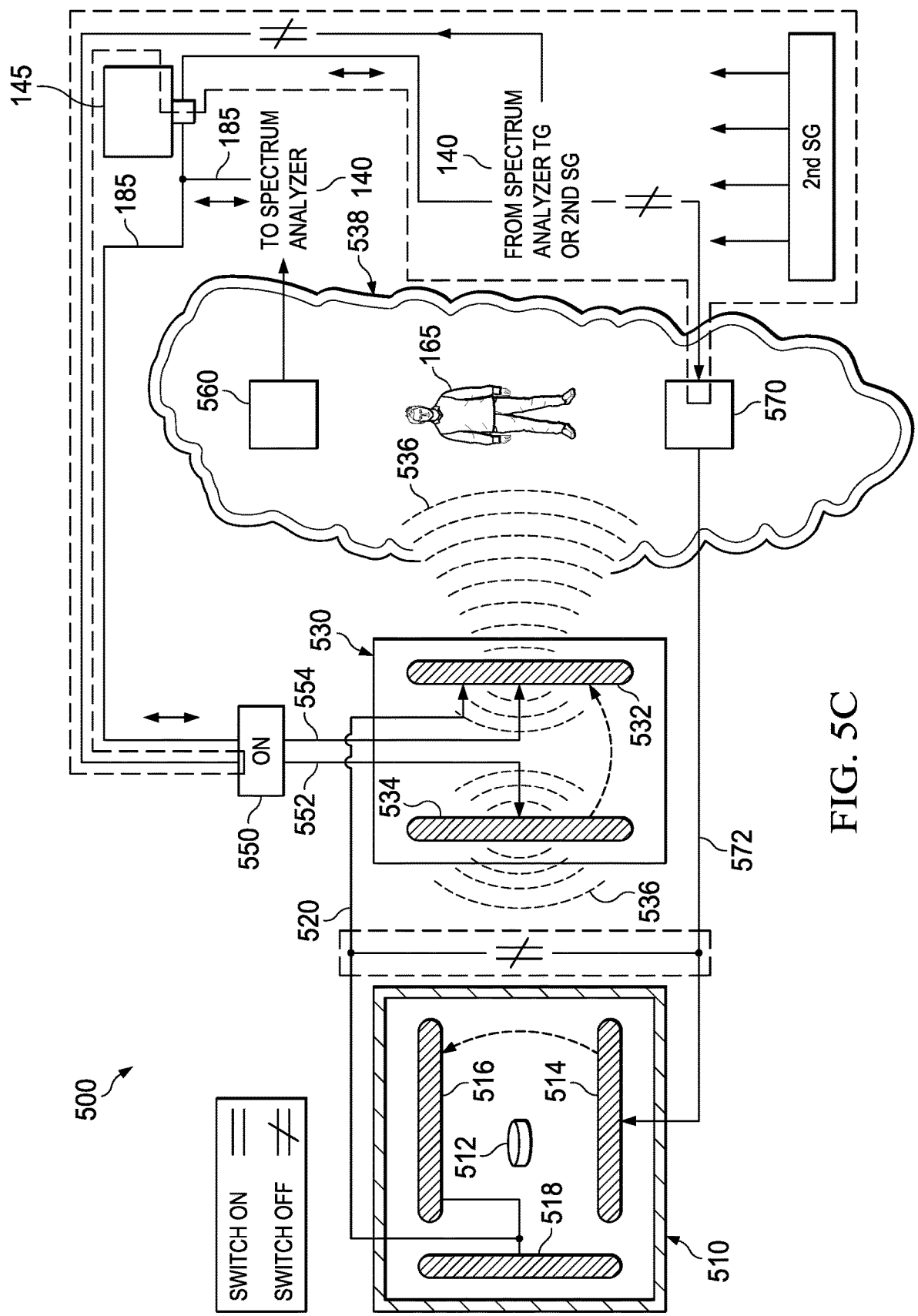
FIG. 5C illustrates a disease detection system in a treatment configuration using ever present reference materials and captured resonant frequencies, according to a specific example embodiment of the disclosure.

FIGS. 5A, 5B, and 5C illustrate a disease (e.g., COVID-19) detection and treatment system 500 according to an example embodiment. A disclosed system 500 may operate in multiple modes, wherein one may detect a disease state and another may treat a disease state. For instance, FIG. 5A represents a detection mode, FIG. 5B represents a treatment mode with extracted resonant frequencies, and FIG. 5C represents a treatment mode with captured resonant frequencies. This multi-mode capability of treatment system 500 is made possible by the addition of antenna arrays with a second separate signal generator and the capability to house a reference material. The spectrum analyzer assembly output that is synced with spectrum analyzer assembly input and upgraded software which is capable of capturing, isolating, extracting, and truncating frequencies and incorporating these truncated frequencies into a database that can compare frequency bands of various substances to detect/diagnose their presence by projecting probability of match. In an embodiment of the detection mode, only a transmitting antenna 560 and receiving antenna 570 are required to isolate, extract and store truncated frequency bands. A patient 165 placed between antennae 560 and 570 may be diagnosed as having the targeted disease or not via comparison with frequency maps in the database. These two antennae are dual mode antennae. For example, in a treatment mode, they serve as feedback antenna 570 and monitoring antenna 560 respectively when switch positions or cable attachments are applied in accordance with prescribed mode methodology. Before detection or treatment may be initiated, reference material resonant frequencies are identified by means of a reference material.

A detection and treatment system 500 which may not require an ever-present reference material (such as illustrated in FIG. 5B) is presented. Instead, resonant frequencies of one or more reference materials may be measured, captured, calculated, extracted, or otherwise determined off-site or beforehand in accordance with an example embodiment, and then recorded manually or digitized and stored in a database within computer 145. Then, a spectrum analyzer assembly 140 may simultaneously generate digitized, calculated, captured, extracted, or measured frequencies of one or more reference materials. The output of a spectrum analyzer assembly tracking generator or separate signal generator 140 and controlled by computer 145 may be implemented as a multi-frequency signal generator or as multiple single-frequency signal generators. The broadcast antenna 520 may comprise antennae 532 and 534 that work together. Antenna 532 may be implemented as a broadband antenna or as multiple single-frequency antennae, which receive(s) resonant frequency information from the output of the spectrum analyzer assembly 140. Antenna 534 may be implemented as a broadband antenna, or as multiple single-frequency antennae for broadcasting resonance generating electromagnetic fields onto subject 165.

In a disease (e.g., COVID-19) detection mode, as shown in FIG. 5A, a disclosed system 500 may include signals that are not modulated and amplified. System 500 may use a multi-step process where a spectrum analyzer assembly's output is pulsing in selected intervals throughout full bandwidth spectra (≤6.0 GHZ), where resonance areas are selected, digitized, and added to a database. In a detection mode, system 500 may include a spectrum analyzer with a tracking generator or a multi-frequency signal generator. If accuracy in a detection mode is not sufficient, the process may be repeated with a smaller bandwidth spectra. If accuracy is sufficient, a frequency map may be built for detection. For example, a target is selected (e.g. SARS-CoV-2 spike protein). A full spectral scan (6 GHz bandwidth) is taken of this protein using a maximum number of points available from the tracking generator (or a separate signal generator). For example, assume the maximum number of points equals 6,000. So, in a bandwidth of 6 GHz, the signal pulses will occur at intervals of 1 MHz. Next, the full spectra is examined to identify areas of resonance. And, assume four (4) areas are found (500 MHz, 850 MHz, 1.0 GHz, 1.7 GHz). These areas are then truncated and used to make a frequency map. The map is added to the database, and diagnostic specificity and sensitivity are tested. Suitable specificity and sensitivity levels of ≥85% are desirable. If testing results are insufficient, the initial span will now be set from 500 MHz to 1.7 GHz instead of the full 6 GHz bandwidth, as the narrower bandwidth would bring speed improvement. Again, using the maximum number of points (6,000), the signal pulses now occur at 200 kHz. The areas of resonance are now re-examined and truncated. The new frequency map would be much more accurate.

In a treatment mode as shown in FIG. 5B, antenna 534 may simultaneously broadcast multiple resonant frequencies onto subject 165, which may impact target cells more effectively than other approaches such as transmitting different single-frequency signals consecutively. In a detection mode, multiple frequency maps may be used simultaneously without amplification or modulation. In contrast, in a treatment mode, signals from the spectrum analyzer assembly output in device 140, may be amplified and modulated via $2^{nd}$ signal generator 550. Feedback antenna 570 provides a feedback signal back to antenna 532. A feedback loop may not be required with sufficient amplification via increased gain and modulation from $2^{nd}$ signal generator 550 and/or via an external amplifier/modulator on the output of the spectrum analyzer assembly 140.

In the treatment mode shown in FIG. 5C, antenna 532 may simultaneously broadcast multiple resonant frequencies onto subject 165, which may impact target cells more effectively than other approaches such as transmitting different single-frequency signals consecutively. In a treatment mode, captured resonant frequency signals from reference material antenna 510 may be amplified and modulated via $2^{nd}$ signal generator 550. Feedback antenna 570 provides a feedback signal back to antenna 532. A positive feedback loop is created in this mode.

In a treatment mode, system 500 may accept multiple frequency maps from a detector and may include a transmitting device such as the tracking generator within a spectrum analyzer or a spectrum analyzer with a separate signal generator 140 and $2^{nd}$ a transmitting device 550 which modulates and amplifies resonant frequency signals from transmitting device 140 or captured reference material 512. As shown in FIGS. 5A, 5B, and 5C, disease detection or treatment system 500 may further comprise feedback antenna 570, which may be connected to a shielded container 510 or transmitting antenna 532 to form a feedback loop. Feedback antenna 570 may be a broadband-capable antenna that receives radiated signal 536 and accordingly generates feedback signal 572. In some embodiments, both generated electromagnetic signals and signals carrying the specific resonances may be radiated, and such radiation may repeat. The repetitive feedback action may amplify resonances specific to a reference material spectrum stored in a database and may quickly cause an external electromagnetic field to reach steady state. Signals from antennae may be first radiated as separate signals. Then, as a result of a feedback loop, signals from antennae may be radiated as mixed signal 536, which is reinforced by received mixed transmission from the feedback antenna(e) and reinforced by mixing with the reference/source material signal. An external electromagnetic field formed between feedback antenna 570 and radiating antenna may also be referred to as near-field zone or area 538 of an antenna array. After reaching a steady state, an external electromagnetic field is considered "tuned," which may be confirmed by use of monitoring antenna 560 and a spectrum analyzer in conjunction with proprietary software (SPAN 32) incorporated in computer 145, which records correlation factors between scans. The electromagnetic field may also be monitored by using an oscilloscope. For example, monitoring antenna 560 (e.g., a broadband antenna) may monitor a spectral profile of signal 536 and then send the profile for analysis to the input of a spectrum analyzer assembly 140, e.g., in terms of component frequencies and magnitudes.

In a treatment mode, system 500 may include a 1 Hz or 4 Hz modulation booster that is adjustable and 1 Hz or 4 Hz modulation frequencies that are adjustable as well. Additionally, in a treatment mode, system 500 may target multiple diseases or targets simultaneously.

In some embodiments, a resonance generating fields technology (RGFIELDS) may use a spectrum analyzer assembly; one or more higher order, multi-solenoidal antennae; a spectral recognition software; and a digital broadband capability in a wavelength ranging between radiofrequency and the low microwave band to identify/extract/truncate spectral signatures unique to a substance (biological or non-biological), to produce a spectral fingerprint. A prime resonant frequency (along with harmonics) specific to a substance and/or disease may be used to build a frequency map. A frequency map may be applied in concert with an algorithm to detect a presence of any disease target. In some embodiments, a disease target may include a SARS-CoV-2. In case of a SARS-CoV-2, a spectral fingerprint of a unique viral protein and/or sequence may be used to build its frequency map.

An RGFIELDS device may scan continuously for multiple targets. An RGFIELDS device may scan a single target individually. A device may provide a binary go/no reading in a time (e.g., seconds) and removal of PPE may not be required. A subject may briefly stand between antennae for scanning. For a business such as a hospital, facial recognition software may be applied to eliminate a contact based log-in including typing or a card swipe login. For a sporting event, concert, or other large public gatherings, no records may be required so that processing may be less restrictive. To accelerate roadside testing, a separate login terminal for HIPAA data entry may be employed. If a subject tests positive for a disease (e.g., a COVID-19), the subject will be given the results and may be directed to quarantine, whereby if the subject tests negative, they will be given results and may be allowed entrance or to return home or to work.

In some embodiments, an RGFIELDS system may detect a presence of a biological or non-biological substance with a scan time of ≤10 seconds, a specificity of ≥95%, and a sensitivity of ≥95%. A software based algorithm may enable electronic storage of relevant frequencies including mapping and a spectral fingerprint. For example, multiple SARS-CoV-2 sequences may be used to form its specific spectral fingerprint. Once mapped and stored electronically in the database, a spectral fingerprint may be transmitted to any RGFIELDS system worldwide. Not only may viruses be detected, but other disease states as well. For examples, a carcinoma including a Glioblastoma Multiforme (Type U-87 MG brain cancer) has been analyzed using a full size prototype to confirm the target with high specificity and sensitivity (detected 100,000 U-87 MG cells in culture). A disclosed system may detect and identify the difference between an empty vial and a vial containing cancer cells or a buffer solution inside a faraday chamber. Software algorithms may be set up to automatically select a spectral fingerprint for detection of a specific disease within a subject.

Processes for Detecting and Treating Diseases Using Disclosed Systems

Figures 6A, 6B:
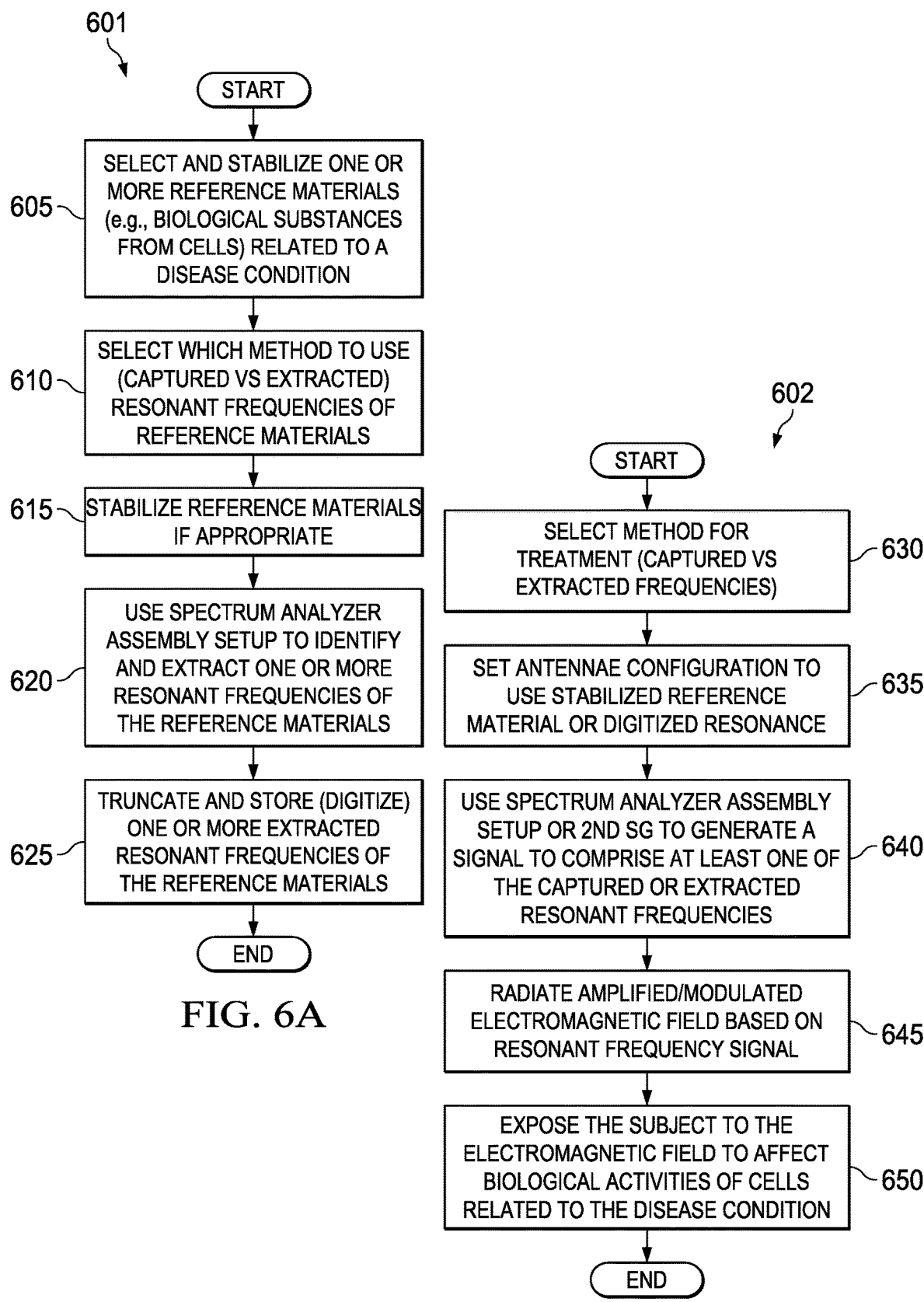
FIG. 6A illustrates multiple processes for administering to a subject having or at risk of having a disease condition with resonance-based electromagnetic radiation, according to a specific example embodiment of the disclosure.
FIG. 6B illustrates a process for treating a disease state present in a subject, according to a specific example embodiment of the disclosure.
Figure 6C:
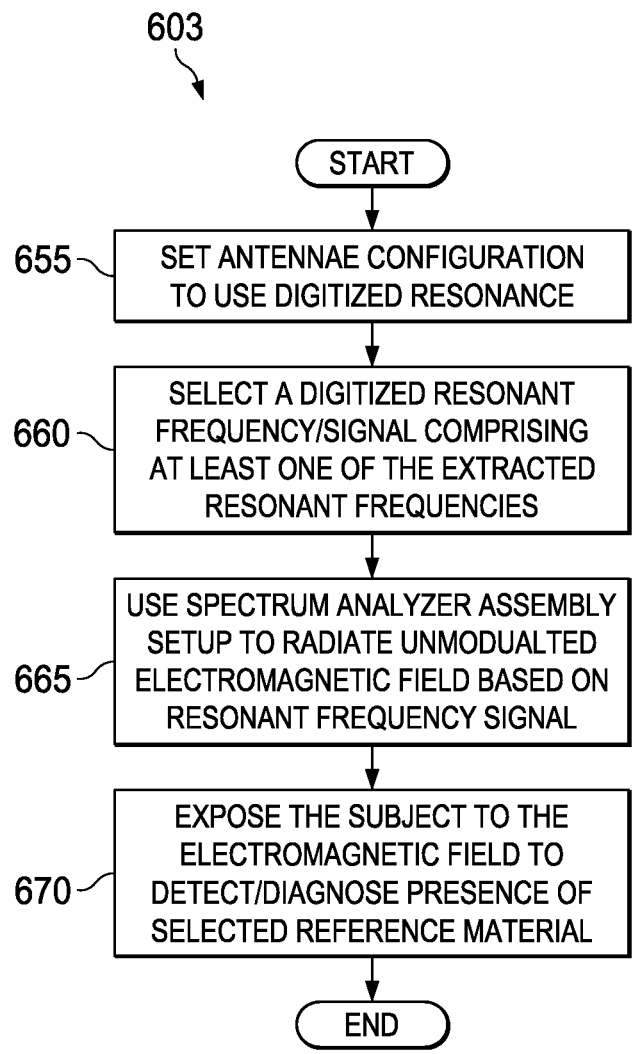
FIG. 6C illustrate a process diagnosing the presence or the absence of a disease in a patient, according to a specific example embodiment of the disclosure.

FIGS. 6A-6C are flowcharts showing processes 601, 602, 603 for administering to a subject having or at risk of having a disease condition with resonance-based electromagnetic radiation, according to an example embodiment (e.g., system 100, 200, 300, 400, 500 as shown in FIGS. 1-5). Process 601, shown in FIG. 6A, may start in action 605, where one or more reference materials related to the disease condition is selected and stabilized. A reference material may be biological substances extracted from cells or other sources or may be synthetic substances (e.g., a synthesized peptide sequence or a synthetic DNA sequence). For example, the reference material may be key to the function, progression, viability, proliferation, continuation, and/or survival of the disease condition. In action 610 a decision is made regarding whether stabilized reference materials are required. If captured frequency method is to be used, in action 615, the selected reference materials are stabilized. In action 620, the spectrum analyzer assembly is used to generate and extract at least one of the selected resonant frequencies. In action 625, one or more of the extracted resonant frequencies are truncated and stored (digitized) in a database of disease specific frequency maps for use in either treatment or detection/diagnostic mode.

FIG. 6B depicts a method 602 for using a disclosed system as a therapeutic to treat a disease. A disclosed method 602 includes a step of selecting 630 which method (captured versus extracted) resonant frequencies of a reference material. A method may include setting 635 an antenna configuration to use stabilized reference materials or digitized resonance. A method 602 may use 640 a spectrum analyzer assembly with tracking generator or a multi-frequency signal generator; or, a broadband signal source to generate a signal containing at least one extracted or captured resonant frequencies respectively. A method 602 may include a step of radiating 645 an amplified and modulated electromagnetic field based on the resonant frequency signal provided to a first broadband antenna. A method 602 includes a step of exposing 650 a patient with the amplified and modulated electromagnetic field to affect biological activities of cells related to a disease.

In action 645, a booster signal comprising a single, low frequency waveform may be optionally generated by the signal generator and provided to a second broadband antenna. In action, an electromagnetic field may be radiated or effectuated jointly based on the resonant frequency signal, the modulated broadband signal, and the booster signal (if present). In action, a patient having or at risk of having a target disease may be administered to by exposing the subject to the resonance generating electromagnetic field to affect biological activities of cells or organisms causing or associated with the disease condition.

As will be understood by those skilled in the art, various embodiments (including those involving additional steps) are contemplated in light of process 602. For example, in an example embodiment, a modulated broadband signal may be simultaneously modulated, in a signal generator, by at least a first waveform at a first frequency and at least a second waveform at a second frequency. The frequencies may be selected based on the application. For example, the first frequency of the first waveform may be about 1 Hz or about 4 Hz, while the second frequency of the second waveform may be less than 1 MHz, less than 100 kHz (e.g., 2.2 kHz), etc.

Embodiments disclosed herein may treat a disease condition with targeted electromagnetic radiation from a suitable apparatus. Process of treatment may include selection, isolation, and stabilization of substances critical to the progression, viability, proliferation, continuation, and/or survival of a particular disease such as cancer, bacterial or viral infections and other maladies. A reference material may provide resonant frequencies (including harmonics) specific to that material which occur within the transmission bandwidth. Measurement and capture of the resonant frequencies may be performed for transmission and amplification of resonant frequency signals. Optionally, resonance may be amplified through a feedback loop, which may or may not include a source of additional amplification. An electromagnetic field developed in the near field zone of an antenna array may be tuned by means of the feedback loop.

As shown in FIG. 6C, a method 603 may include diagnosing the presence or the absence of a disease in a patient 165. A method 603 may include a step setting the antenna configuration to accept digitized resonance 655. In action 660, one or more reference materials (e.g., biological substances from cells) that are related to a disease condition are selected. In some embodiments, a reference material may not be needed, but instead digitized spectra stored in a database may be used. A method 603 may include a step of using 665 a spectrum analyzer assembly setup to radiate an unmodulated electromagnetic field based on resonant frequency signal and a step of exposing 670 a patient to an electromagnetic field to detect presence or absence of a disease (e.g., COVID-19) matching a selected reference material.

As illustrated in the figures, disease testing systems disclosed herein (e.g., 100, 200, 300, 400 and 500) use a device that generates an electromagnetic field to exposes a disease and detects resonant frequencies of the disease. A pulse antenna may be used to radiate the electromagnetic field onto the patient, and a receiving antenna may be used to collect information of the electromagnetic field (e.g., changes in an amplitude of the electromagnetic field). Changes in the detected electromagnetic field may indicate the presence of a target disease in the patient. That is, if a patient carries the disease, the result will return positive; otherwise, the result will return negative. To detect a disease such as COVID-19, the resonant frequencies for the disease is determined accurately. The more accurate the isolated resonant frequency; the less scan time is required to confirm the presence or absence of the virus. In an embodiment, a testing result may be returned in a matter of seconds (e.g., 30 seconds or less), which can be classified as "real time" compared to other existing testing technologies.

According to an embodiment, developing a diagnostic method may begin with selecting a particular disease to be targeted (e.g., COVID-19). Next, a primary frequency (and harmonics) of the target disease may be isolated. Resonant frequencies for the target may be isolated based on live patient methodology or a specific target methodology. For example, following a live patient methodology, a first group of infected patients (e.g., 10 person cohort) and a second group of uninfected patients (e.g., 10 person cohort) may be exposed to the same testing conditions, and the differences in their respective results (e.g., difference in amplitude of electromagnetic field at certain frequencies) may be used to isolate the resonant frequencies. For another example, following a specific target methodology, relevant target substance(s) or material(s) for a disease, such as targeted oligonucleotides and proteins specific to the disease (proteins, DNA, mRNA, etc.), may be identified, e.g., via experts from the scientific and medical communities. A certain quantity of the identified target(s) may then be secured and prepared for determining resonant frequencies.

In an embodiment, proteins, DNA, and/or mRNA, etc. specific solely to COVID-19 are identified to provide appropriate targets. For instance, targeted reference materials may include: spike protein responsible for viral attachment to angiotensin converting enzyme (ACE) receptors on the epithelial cells in the lung; novel Furin cleavage sites in the viral polyprotein that appear to be unique to COVID-19; protein fragments from these sequences and viral RNA sequences that encode these regions, which can be synthesized commercially. To the extent that the resonant frequencies for different variants or mutations of COVID-19 would differ, the resonant frequencies may be individually ascertained. Further, selecting certain core reference materials that do not vary; may help isolate generally applicable resonant frequencies for COVID-19.

Frequency isolation may be done in a Faraday chamber, which helps eliminate background electromagnetic radiation or noise. The system may be configured using properly configured components (antennas, test and measurement equipment, etc.) to measure various parameters such as an amplitude of resonance(s). In an embodiment, a testing system captures electromagnetic frequencies specific to a particular target(s) and uses a pulsing antenna to radiate an electromagnetic field, which is "tuned" to the selected target's resonant frequencies. The electromagnetic field is sometimes not amplified to prevent distortion of signal. When a patient or substance is exposed to an appropriately tuned electromagnetic field, electromagnetic resonance is induced within the target(s) which significantly affects proliferation and viability of that disease. Additional details of a system for determining the resonant frequencies and other aspects are disclosed in U.S. Pat. Nos. 9,610,458 and 10,279,190, both titled "Treating Disease with Resonance Generating Electromagnetic Fields," but it should be understood that modifications and adaptations are made for applications disclosed herein. In an embodiment, live infected patients may be scanned using frequencies over a broadband range (e.g., 9 kHz-6.7 GHz), live uninfected patients may be scanned over the same broadband range, and an empty background may be scanned over the same broadband range. Next, radio or microwave frequency resonance of infected patients may be compared to that of uninfected patients. Alternatively, or additionally, radio or microwave frequency resonance of infected patients may be compared to that of the empty background. Alternatively, or additionally, radio or microwave frequency resonance of uninfected patients may be compared to that of the empty background. Alternatively, or additionally, targeted oligonucleotides and proteins specific to a disease (e.g., proteins, DNA, mRNA, etc.) may be compared to that of an empty background.

The accuracy of primary frequency (and harmonics) determination may be refined using a spectrum analyzer with tracking generator and/or network analyzer. In an embodiment, the accuracy of an isolated frequency peak is increased using a moderately wide resolution bandwidth (RBW) of 10-100 Hz. Alternatively, or additionally, the accuracy of that isolated frequency peak may be refined by using a smaller RBW of 1 Hz until an actual frequency is determined to be within two or more significant digits. Once a primary frequency and related harmonics are isolated, a frequency map may be developed for a particular disease and incorporated into a diagnosis software for field testing. Simultaneously, the software's existing database may be expanded to include patient data; test results, etc. In an embodiment, a frequency map may be transmitted electronically, for example, via a USB or thumb drive, via streaming, and/or via email attachment. It may be shared across geographical locations to enable quicker and more accurate testing in places (without having to first develop the frequency map locally in the testing site).

In an embodiment, the testing system is configured to broadcast only resonant frequencies instead of a broad frequency spectrum to detect a disease. For example, a multi-frequency radio frequency (RF) signal generator may be used with set points at a primary resonant frequency and harmonics, which are controlled via an integrated frequency map. For another example, an arbitrary wave form (ARB) generator may be used with set points at a primary resonant frequency and harmonics, which are controlled via an integrated frequency map.

During development of the disclosed testing systems, test accuracy using live patients and/or specifically targeted materials in a shielded facility may confirm efficacy of testing system. For example, a baseline is established without patient or targets in the chamber. Patients or sample material may be scanned for presence of the target disease. The accuracy of diagnosis may be confirmed (e.g., rates of correct diagnosis, false positives, and false negatives). In some cases, if the percentage of correct diagnosis is low (e.g., less than 95%), parameters such amplitude may be adjusted to increase accuracy. Otherwise testing may move on to an open environment if the percentage of correct diagnosis is high (e.g., 95% or higher). Background EMI is filtered out to enable operations outside of a Faraday and/or Anechoic chamber. In an embodiment, a series of filters are applied to remove background radiation to facilitate operation of the testing system in an open environment (not in a shielded facility). The filtering is tuned to achieve appropriate balancing between sensitivity and accuracy (e.g., too much filtering may miss the detection of harmonic frequencies, but too little filtering may leave in significant background EMI). Enough patients should be tested to confirm statistically significant results in the open environment. Live field tests are conducted with patients and/or targeted materials. Portable point of care and point of entry devices may be deployed. With component miniaturization, handheld devices may be deployed for field use.

The present disclosure describes many embodiments. For example, it includes embodiments for isolating primary frequency (and harmonics) of a targeted disease, which may be done via live patients or via target reference materials. It includes embodiments for increasing accuracy of isolated frequencies and improving success rate of detection (e.g., less than 5% false positive or false negative results). It includes embodiments for constructing a resonant frequency map for incorporation into diagnostic and/or therapeutic devices such as a POC device, point of entry device, handheld point of care device for field use, a resonance field based therapeutic device. It includes embodiments for transmitting resonant frequency maps electronically, for example, via a USB or thumb drive, via streaming, and/or via email attachment. It includes embodiments for facilitating simultaneous detection of multiple diseases (e.g., broadcasting different resonant frequencies to detect different diseases). It includes embodiments for diagnosing presence of disease remotely without need for costly testing supplies or PPE. It includes embodiments for diagnosing presence of disease with portable devices such as a handheld device.

Compared with existing testing technologies for COVID-19, benefits of the disclosed technology include significant decrease in test time plus exponential increase in testing capacity. Some embodiments eliminate the need for PPE by medical personnel conducting tests. Further, testing results can be shared electronically and immediately with any agency and the public. Costs per test may be lowered.

EXAMPLES

Example 1. The Process of Forming Spectral Fingerprints Using Truncated Frequency Maps In an embodiment, the process of forming a frequency map with spectral fingerprint(s) with the RGFIELDS technology uses at least three steps: Conduct a full bandwidth spectral scan; review narrow segments of the full bandwidth scan to identify distinctive areas of resonance; and truncate the distinctive areas to add to the frequency map, which contains the spectral fingerprints. Should specificity be insufficiently low, the process is repeated now using a more narrow frequency range that includes only the lowest resonance area to the highest to increase accuracy further. In initial experiments, a small prototype was used to test concept capabilities. Antennae in this unit were mounted in a small container approximately 15" apart. This system used a spectrum analyzer with a tracking generator and the upgraded system software. Nine (8) target substances (tap water, sugar, rock salt, buckwheat, sunflower oil, rice, breadcrumbs, fruit juice) were selected and placed into identical 500 ml plastic containers. Full band spectral scans were taken for five (5) cycles for each substance plus an empty 500 ml plastic container. And the five (5) scans for each substance were averaged and the spectra examined for areas of resonance. Once the resonant areas were determined, the frequencies were manually selected, and the selections used to form truncated frequency maps for each substance, which were then incorporated into a common database. The system was placed in the open (outside a Faraday chamber). The software was set for continuous mode and multiple substances. In this setting, the system sequentially broadcasts the frequencies for each substance and compares the radiated signals (reflected, refracted, through and around the substance). When all scans are complete, the broadcast repeats the sequence. In a run, cycle time to complete the sequence for the eight (8) substances plus the empty container was 10.2 seconds. The system was started and testing commenced. Protocol was to first place the empty plastic container between the two antenna and wait for a reading. Once the reading was given, the next sample was placed where a reading was awaited, and so forth. Results were exceedingly accurate. Each substance was tested twenty (20) times on different days where the system reliably detected all substances every time with the exception of the breadcrumb sample. In this particular case, the system confused breadcrumbs for sugar 50% of the time. The frequency map for breadcrumbs was redone using more narrow bandwidths and then the system correctly identified breadcrumbs reliably. With system capability having been proven, a full scale unit has been made, which embodiments herein reflect.

Figure 7:
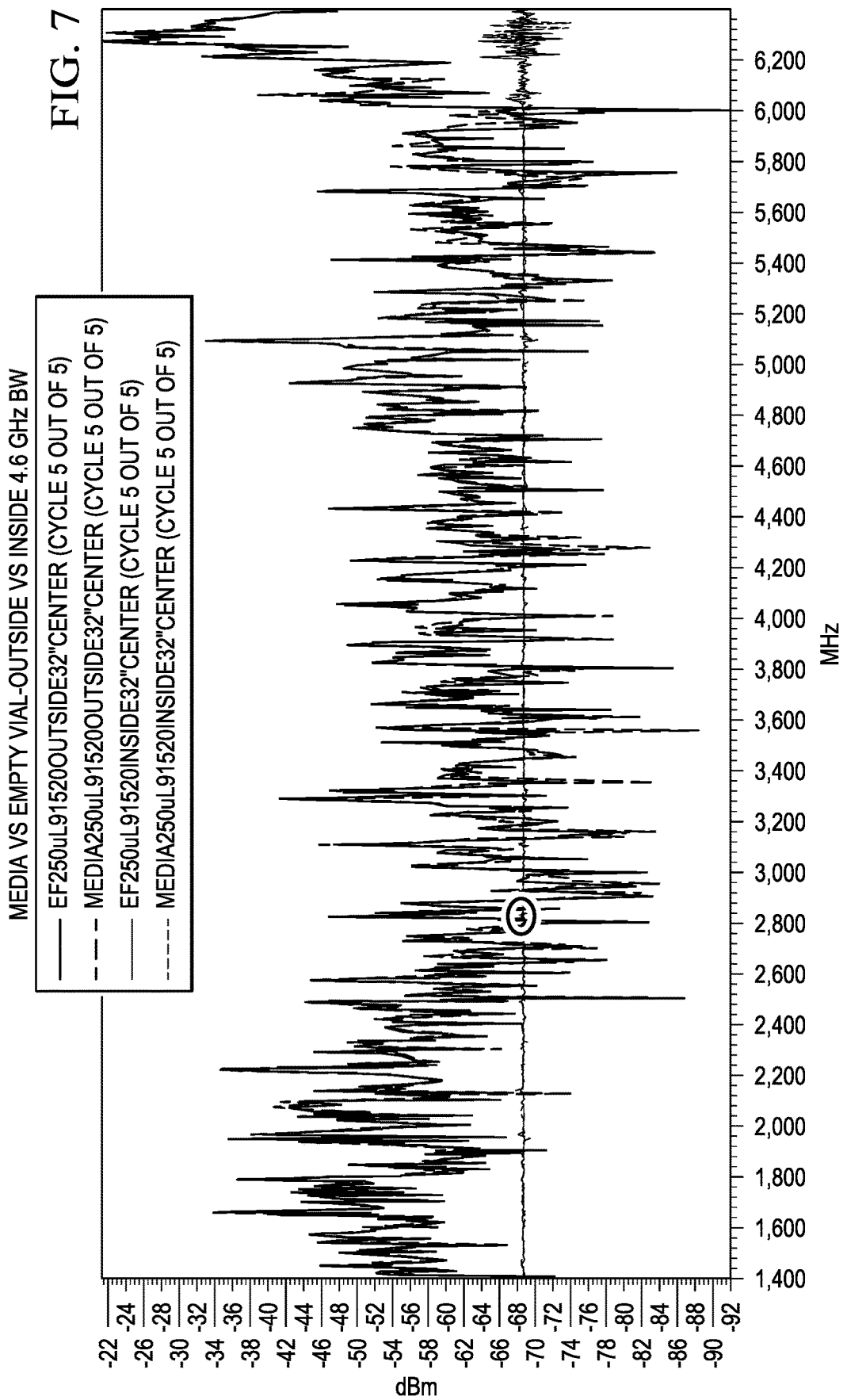
FIG. 7 illustrates a full spectral bandwidth of the empty vial vs the media vial taken both inside and outside the shield room, according to a specific example embodiment of the disclosure.
Figure 8:
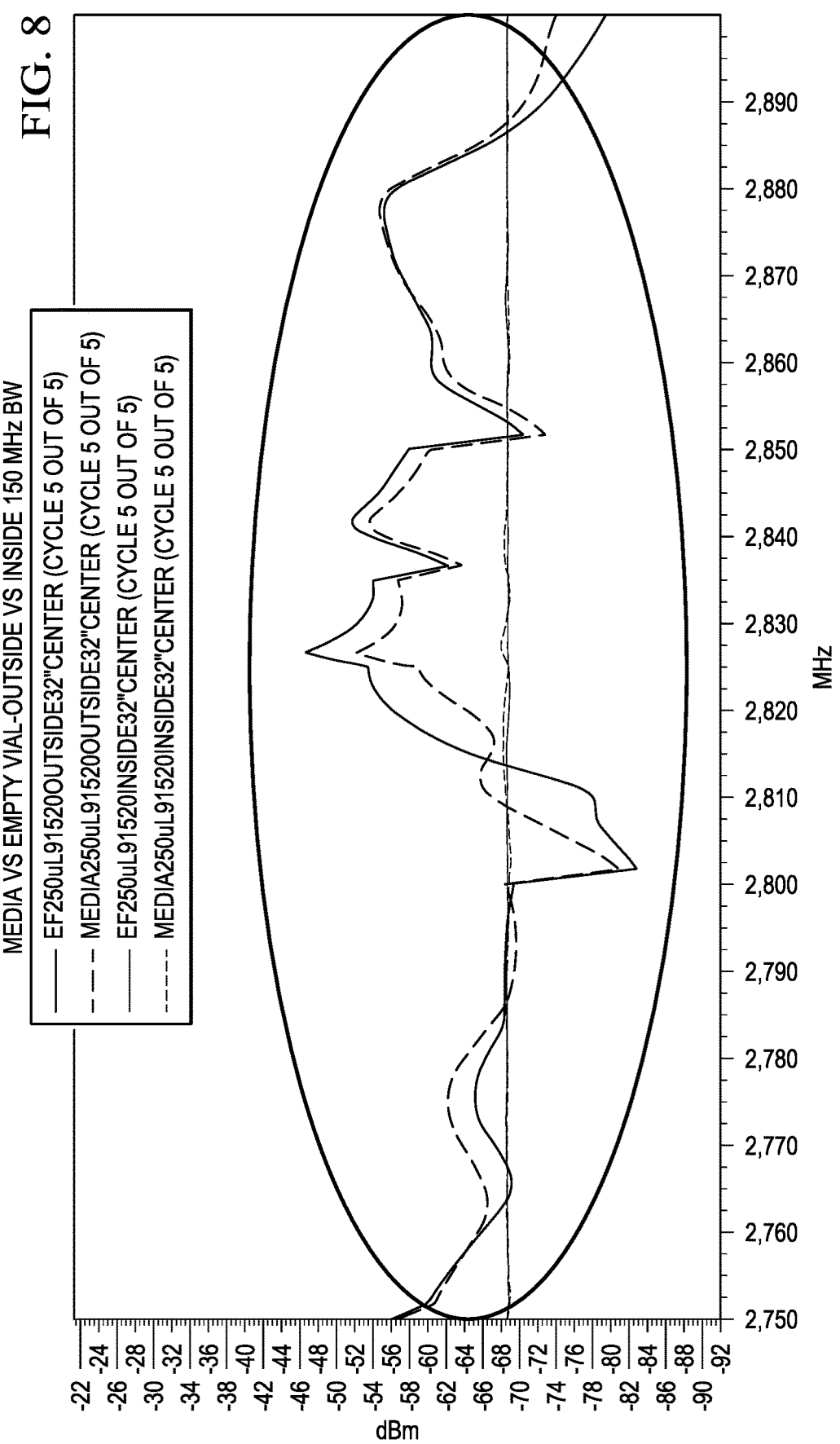
FIG. 8 illustrates a closer look at a smaller segment of the full spectral bandwidth from FIG. 7, according to a specific example embodiment of the disclosure.

Example 2. Comparing Spectra of Identical Substances Outside Vs Inside a Shield Chamber Spectra were obtained of an empty 250 μL vial and a media filled 250 μL vial when inside and later outside of a shield chamber. The device used was a full scale prototype wherein transmitting antenna and receiving antenna were placed 32" apart, both inside a shield chamber and outside a shield chamber. This comparison was conducted to illustrate the effect of outside interference on spectra from identical targets. FIG. 7 shows a full spectral bandwidth of the empty vial vs the media vial taken both inside and outside the shield room, whereas FIG. 8 is a closer look at the smaller band width (circle on FIG. 7) of that same spectra. In FIGS. 7 and 8, the oval circles cover a 150 MHz bandwidth of the same area. This area was specifically selected since the spectra of both the empty and media vials are the same taken inside the shield room, thereby enabling examination of the effect of outside interference on the spectra of target substances. Truncated frequency maps were produced in accordance with accepted protocol. Specificity inside the shield chamber was 100% for five (5) iterations tested. Testing outside showed specificity of 67%, which was understandably lower. In some embodiments, slight amplification of the transmitted signals from spectrum analyzer assembly output or filters to partially remove background noise would help increase specificity to higher levels.

Example 3. Specificity and Sensitivity Results when Detecting the Presence of U-87 MG Brain Cancer Cells when Compared with Two Other Target Substances Results using a full scale prototype to detect non-biological substances were satisfactory. And testing for the presence of a live biological substance was done. Glioblastoma brain cancer cells (Type U-87-MG) were selected since these cells and the faraday chamber were readily available at the test facility. Studies were conducted to determine specificity and importantly, sensitivity rates for minute quantities of target substances (more specifically, a quantity of U-87-MG cancer cells that may be found in a human body afflicted by this disease). So, to proceed, a standard protocol was followed to form the truncated frequency maps which would determine accuracy, via first a full bandwidth scan, followed by narrow bandwidth review, then followed by selection/truncation to form the frequency maps, both outside the chamber and inside the chamber.

Figure 9:
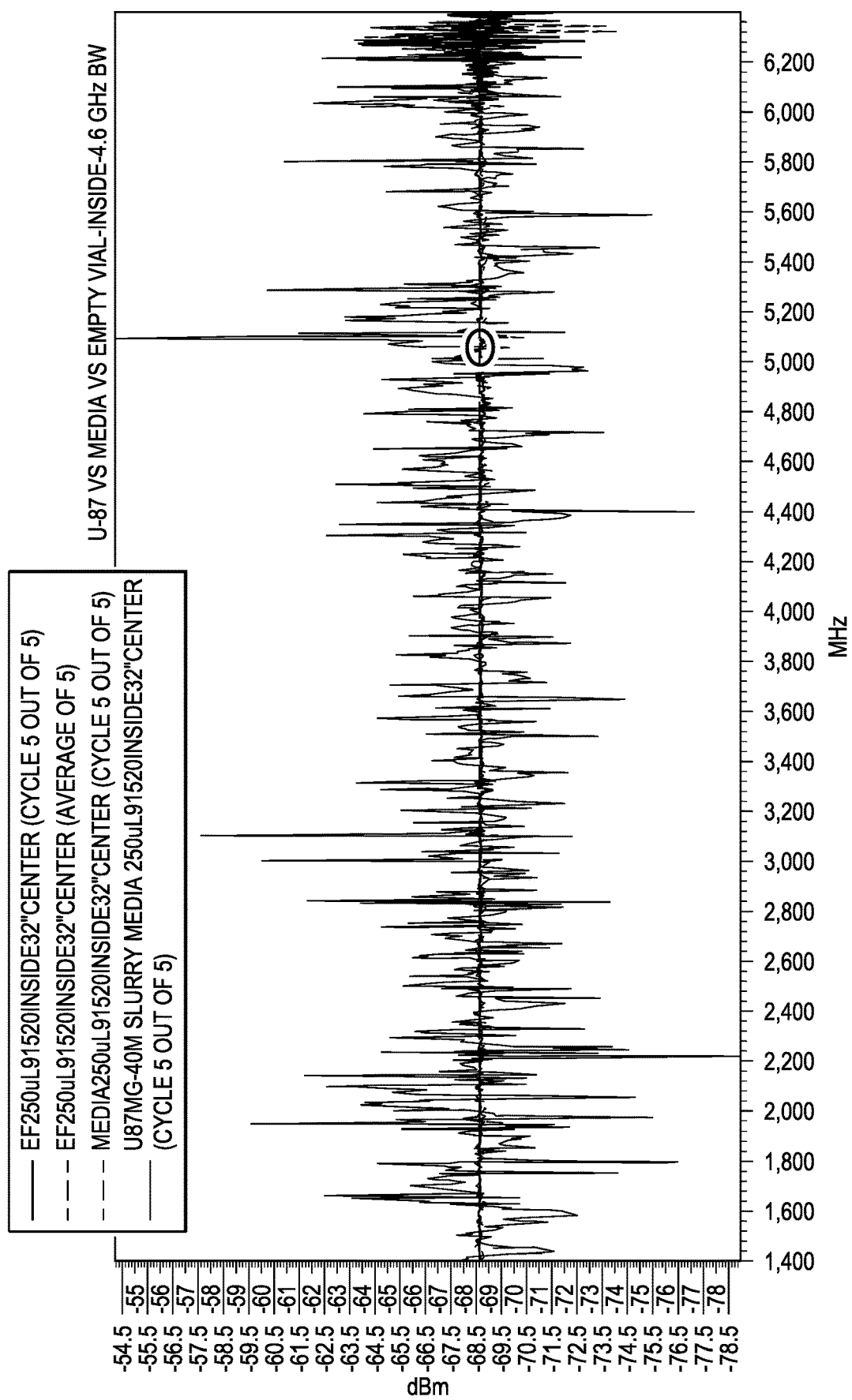
FIG. 9 illustrates a full bandwidth spectra of an empty 250 µl vial vs a media filled 250 µl vial vs a 250 µl vial with 40 million, according to a specific example embodiment of the disclosure.
Figure 10:
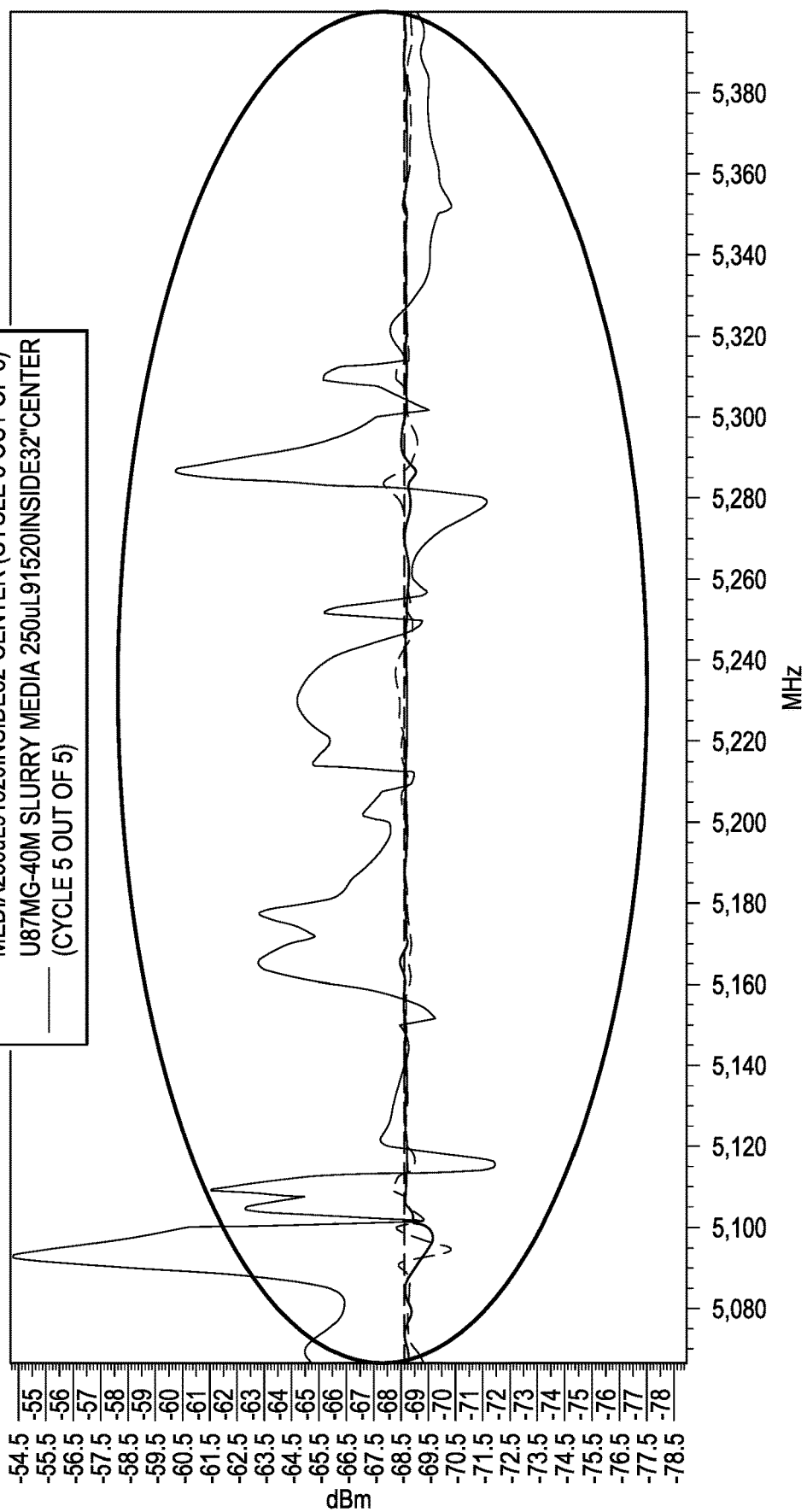
FIG. 10 illustrates a narrow bandwidth portion of the same spectra shown in FIG. 9, according to a specific example embodiment of the disclosure.

FIG. 9 illustrates full bandwidth spectra of an empty 250 μl vial vs a media filled 250 μl vial vs a 250 μl vial with 40 million, U-87-MG cancer cells observed inside a shield chamber and an area of interest (see encircled frequency range), according to a specific example embodiments of the present disclosure. FIG. 10 illustrates a more narrow bandwidth portion of the same spectra shown in FIG. 9, an empty 250 μl vial vs a media filled 250 μl vial vs a 250 μl vial with cancer cells observed inside a shield chamber, according to a specific example embodiments of the present disclosure. The area in FIG. 10 is then truncated along with several other areas of interest associated with the same target substance and added to the frequency map as one of several spectral fingerprints that can then be used to detect the presence of either particular substance in a much shorter period of time than running a complete scan (i.e., seconds rather than minutes). The truncated spectral fingerprint is digitized and can be used to treat a disease more effectively. After extraction/truncation/digitization of the spectral fingerprint occurs, the frequency map is then transmitted to any device containing the appropriate software worldwide instantaneously via email, streaming, etc.

Figure 11:
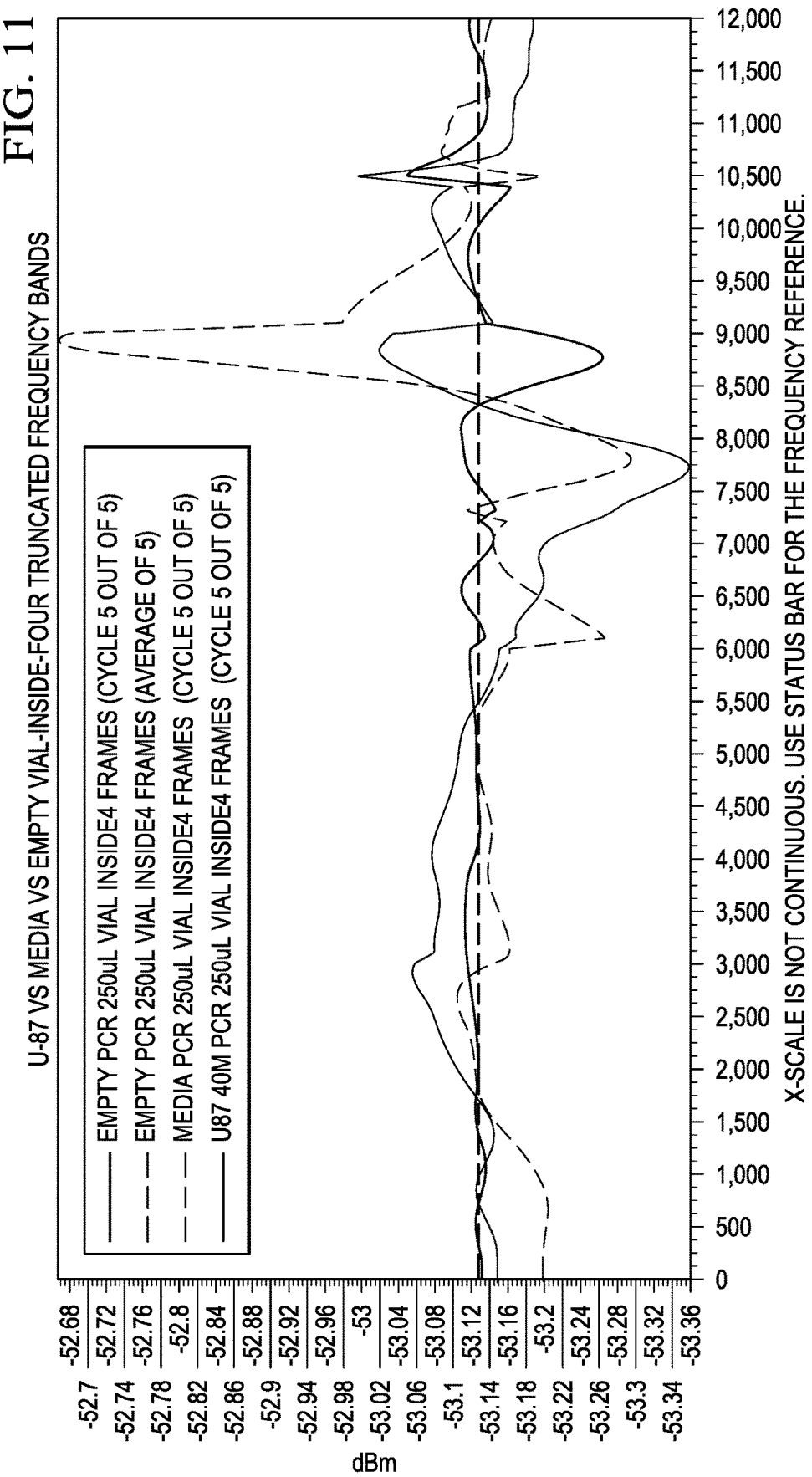
FIG. 11 illustrates four truncated spectra extracted from four different narrow bandwidths of the full bandwidth spectra from FIG. 9, according to a specific example embodiment of the disclosure.
Figure 12:
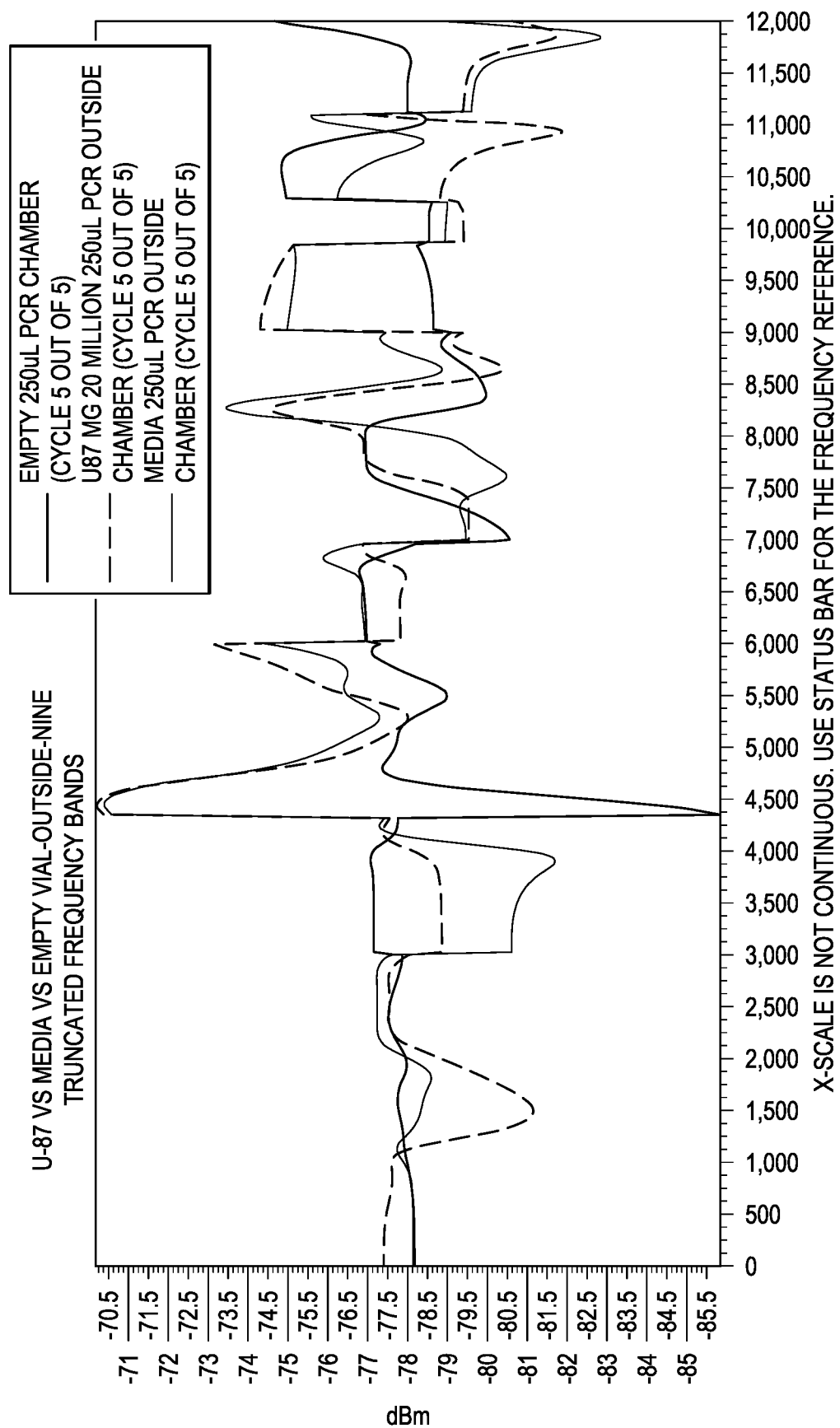
FIG. 12 illustrates nine truncated spectra extracted from nine different narrow bandwidths of a full bandwidth spectra of an empty 250 µl vial vs media filled 250 µl vial vs a 250 µl vial with cancer cells observed outside a shield chamber, according to a specific example embodiments of the disclosure.

A technique for better highlighting spectral differences is to select a reference spectra and subtract that reference from all other spectra involved. This technique enhances differences and as such was used in FIG. 11 which illustrates four (4) truncated spectra extracted from four (4) different narrow bandwidths of the full bandwidth spectra shown in FIG. 9 an empty 250 μl vial vs media filled 250 μl vial vs a 250 μl vial with cancer cells observed inside a shield chamber, wherein the average of five (5) spectral scans of the empty vial has been subtracted from the portrayed single scans of each substance to better highlight differences, according to a specific example embodiments of the disclosure. Testing commenced comparing specificity results inside the Faraday chamber between the empty vial, the media filled vial and the cancer filled vial holding 40 million cancer cells. Substances were exchanged repeatedly with five (5) iterations and each time detection was 100% accurate with ≥95% probability of match shown each time. Next sensitivity tests were conducted using various decreasing levels of U-87 MG cancer cells. The tests would be similar to the first series but this time only three (3) iterations were conducted for each cancer cell concentration. The targets contained respectively 15 million cells, 5 million, 1 million and 100,000 U-87 MG cancer cells. In testing to detect the presence of each target (empty vial, media filled vial and each cancer cell vial); inside the faraday chamber, the highest sensitivity achieved was 99.75% (40,000,000−100,000=39,900,000÷40,000,000 or 99.75%). The antennae were now taken outside the shield room and setup identically to the inside configuration. The same repetitive tests were run. While the device reliably detected the presence of 40,000,000 U-87 MG cancer cells every time; sensitivity less accurate; where the lowest level of accurate detection was 1,000,000 U-87 MG cells at 97.5% (40,000,000−1,000,000=39,000,000÷40,000,000 or 97.5%). Moreover, while specificity remained high detecting the presence of cancer cells, the system could not reliably differentiate the media filled vial from the empty vial, as specificity dropped to approximately 50%. FIG. 12 illustrates nine (9) truncated spectra extracted from nine (9) different narrow bandwidths of the full bandwidth spectra of an empty 250 µl vial vs media filled 250 µl vial vs a 250 µl vial with cancer cells observed outside a shield chamber, according to a specific example embodiments of the present disclosure.

Example 4. Comparing Spectra of JF Startari (a Person) Vs Spectra of a 50 mL Media Filled Flask Inside a Shield Chamber A full scan spectra of media filled flask is taken by a device having a bandwidth of 6 GHz, which pulse broadcast (digital instead of analog) from an SA with TG having bandwidth of 6.5 GHz. This study was taken inside a Faraday chamber to determine the effectiveness of the system in detecting the difference between spectra formed by an individual and a media filled 50 ml flask. Transmitting and receiving antenna separation was set at 32". Due process was followed where more narrow portions of the full bandwidth spectra were examined and areas of significant resonance were selected to form a truncated frequency map that was incorporated in the database. In this example, 5 truncated frequency bands make up the frequency map. FIG. 13 shows the truncated spectra from cycles 4 and 5 of 50 ML of media in a Styrofoam container vs the truncated spectra from and cycles 3 and 4 of JF Startari (a person). Substantial differences between the two spectra enable a very high specificity and quick detection time since the bandwidths of each truncated spectra a very small. As can be readily observed, slight spectral differences in the JF Startari scans are present, where the media filled flask spectra completely overlap. The spectral differences are thought to be associated with breathing and slight movement which changes volume/reflective/refractive signals. Despite these minor changes in the JF Startari spectra, specificity in detecting the presence of media or JF Startari was very high inside the chamber; where five (5) repeated exchanges correctly detected the target each time. A decision was made to use the frequency maps generated in the shield room to determine the specificity of the equipment outside the chamber. Specificity of the equipment still showed 100% detection reliability. However, the probability of match calculated by the system software dropped from ≥95% inside the chamber to about 88%, thereby confirming the effect of outside interference on the process.

Spectra of both an empty vial and a media containing vial were obtain both outside and inside a Faraday chamber (shield room). The obtained spectra are shown in FIG. 9. Specificity and sensitivity were much better in detecting minute quantities of a target material when using the shield room compared with operating in the open.

As will be understood by those skilled in the art who have the benefit of the instant disclosure, other equivalent or alternative compositions, devices, methods, and systems for resonance-based disease treatment can be envisioned without departing from the description contained herein. Accordingly, the manner of carrying out the disclosure as shown and described is to be construed as illustrative only.

Persons skilled in the art may make various changes in the nature, number, and/or arrangement of parts or steps without departing from the scope of the instant disclosure. For example, the size of a device and/or system may be scaled up or down to suit the needs and/or desires of a practitioner. Each disclosed method and method step may be performed in association with any other disclosed method or method step and in any order according to some embodiments. Where the verb "may" or "can" appears, it is intended to convey an optional and/or permissive condition, but its use is not intended to suggest any lack of operability unless otherwise indicated. Where open terms such as "having" or "comprising" are used, one of ordinary skill in the art having the benefit of the instant disclosure will appreciate that the disclosed features or steps optionally may be combined with additional features or steps. Where "based on" or "based upon" is used, one of ordinary skill in the art having the benefit of the instant disclosure will appreciate that it means one thing is dependent at least in part on another thing, directly or indirectly, exclusively or non-exclusively. Such option may not be exercised and, indeed, in some embodiments, disclosed systems, compositions, apparatuses, and/or methods may exclude any other features or steps beyond those disclosed herein. Elements, compositions, devices, systems, methods, and method steps not recited may be included or excluded as desired or required. Persons skilled in the art may make various changes in methods of preparing and using a composition, device, and/or system of the disclosure.

Also, where ranges have been provided, the disclosed endpoints may be treated as exact and/or approximations as desired or demanded by the particular embodiment. Where the endpoints are approximate, the degree of flexibility may vary in proportion to the order of magnitude of the range. For example, on one hand, a range endpoint of about 50 in the context of a range of about 5 to about 50 may include 50.5, but not 52.5 or 55 and, on the other hand, a range endpoint of about 50 in the context of a range of about 0.5 to about 50 may include 55, but not 60 or 75. In addition, it may be desirable, in some embodiments, to mix and match range endpoints. Also, in some embodiments, each figure disclosed (e.g., in one or more of the examples, tables, and/or drawings) may form the basis of a range (e.g., depicted value+/−about 10%, depicted value+/−about 50%, depicted value+/−about 100%) and/or a range endpoint. With respect to the former, a value of 50 depicted in an example, table, and/or drawing may form the basis of a range of, for example, about 45 to about 55, about 25 to about 100, and/or about 0 to about 100.

All or a portion of a device and/or system for disease treatment may be configured and arranged to be disposable, serviceable, interchangeable, and/or replaceable. These equivalents and alternatives along with obvious changes and modifications are intended to be included within the scope of the present disclosure. Accordingly, the foregoing disclosure is intended to be illustrative, but not limiting, of the scope of the disclosure as illustrated by the appended claims.

Headings (e.g., Title, Background, and Detailed Description) are provided in compliance with regulations and/or for the convenience of the reader. They do not include and should not be read to include definitive or over-arching admissions as to the scope and content of prior art or limitations applicable to all disclosed embodiments.

The invention claimed is:

1. An electromagnetic resonance-based disease detecting system comprising:
   (a) a signal generator configured to generate a resonant frequency signal that carries at least one frequency at which reference materials relate to a disease condition resonate;
   (b) a radiating antenna electronically connected to the signal generator and configured to radiate a subject with an electromagnetic field based on the resonant frequency signal, wherein radiating the subject with the electromagnetic field generates a subject spectrum;
   (c) a receiving antenna configured to receive the subject spectrum;
   (d) a spectrum analyzer assembly comprising one of a spectrum analyzer with an internal tracking generator or a spectrum analyzer with a separate signal generator, the spectrum analyzer assembly electronically connected to the receiving antenna and configured to receive the subject spectrum from the receiving antenna; and
   (d) a processor connected to the spectrum analyzer assembly, the radiating antenna, and the receiving antenna, wherein the processor is configurable to:
      (i) control the resonant frequency signal generated by the spectrum analyzer assembly;
      (ii) control the electromagnetic field radiated from the radiating antenna; and
      (iii) control the spectrum analyzer assembly to determine one of an absence and a presence of the disease condition resonate.

2. The electromagnetic resonance-based disease detecting system according to claim 1, wherein the disease condition resonate comprises a virus or its specific nucleotides selected from the group consisting of a severe respiratory syndrome coronavirus, a virus, an RNA virus, a SARS-CoV-2, a Middle East Respiratory syndrome-related coronavirus (MERS-CoV), a human coronavirus NL63 (HCoV-NL63), a human coronavirus HKU1 (HCoV-HKU1), a human coronavirus OC43 (HCoV-OC43), a human coronavirus 229E (HCoV-229E), and a combination thereof.

3. The electromagnetic resonance-based disease detecting system according to claim 2, wherein the severe respiratory syndrome coronavirus is a strain of COVID-19.

4. The electromagnetic resonance-based disease detecting system according to claim 1, further comprising a patient testing station comprising a frame that supports the radiating antenna and the receiving antenna.

5. The electromagnetic resonance-based disease detecting system according to claim 4, wherein the patient testing station further comprises a communication device comprising one or more of a computer terminal, an audio communicator, and a video communicator.

6. The electromagnetic resonance-based disease detecting system according to claim 4, wherein the frame has a height that is tall and wide enough to accommodate a standing patient.

7. The electromagnetic resonance-based disease detecting system according to claim 4, further comprising:
   a remote monitoring station comprising one or more computer terminals and one or more user interfaces and
   a patient check-in station comprising one or more computer terminals and one or more user interfaces, wherein the patient check-in station is in electronic communication with the remote monitoring station, and wherein the remote monitoring station is in electronic communication with the patient testing station.

8. The electromagnetic resonance-based disease detecting system according to claim 1, further comprising a cart configured to support and transport the spectrum analyzer assembly, the radiating antenna, and the receiving antenna,
   wherein the radiating antenna comprises a radiating antenna connector that permits the radiating antenna to be stationed at a distance from about 1 foot to about 10 feet from the cart while maintaining the electronic connection with the signal generator and the processor, and
   wherein the receiving antenna comprises a receiving antenna connector that permits the receiving antenna to be stationed at a distance from about 1 foot to about 10 feet from the cart while maintaining the electronic connection with the spectrum analyzer assembly and the processor.

9. The electromagnetic resonance-based disease detecting system according to claim 1, further comprising a container defining a void for holding one or more of a housing, the spectrum analyzer assembly, the radiating antenna, the receiving antenna, and the processor within the container,
   wherein the container is configured to transport one or more of the housing, the signal generator, the radiating antenna, the receiving antenna, the spectrum analyzer assembly, and the processor from a first location to a second location,
   wherein the radiating antenna comprises a radiating antenna connector that permits the radiating antenna to be stationed at a distance from 1 foot to 10 feet from the container while maintaining the electronic connection with spectrum analyzer assembly output and the processor, and
   wherein the receiving antenna comprises a receiving antenna connector that permits the receiving antenna to be stationed at a distance from 1 foot to 30 feet from the container while maintaining the electronic connection with the spectrum analyzer assembly input and the processor.

10. The electromagnetic resonance-based disease detecting system according to claim 9, further comprising one or more rechargeable batteries electronically connected to one or more of the radiating antenna, spectrum analyzer assembly, the receiving antenna, and the processor,
    wherein the one or more rechargeable batteries are configured for supplying power to the spectrum analyzer assembly, the radiating antenna, the receiving antenna, and the processor.

11. The electromagnetic resonance-based disease detecting system according to claim 10, wherein the container comprises one or more straps that are attached to a face of the container, wherein the one or more straps are configured to secure the container to an operator.

12. The electromagnetic resonance-based disease detecting system according to claim 1, further comprising a cart configured to support and transport, antenna supports, positive/negative test result lights, the radiating antenna, the receiving antenna, and the spectrum analyzer assembly,
wherein the radiating antenna is supported by a stand and comprises a radiating antenna connector that permits the radiating antenna to be stationed at a distance from about 1 foot to about 10 feet from the cart while maintaining the electronic connection with the output of the spectrum analyzer assembly, and the processor,
wherein the system processor comprises an algorithm that activates automatic test result lights attached to the radiating and receiving antenna, and
wherein the receiving antenna is supported by a stand and comprises a receiving antenna connector that permits the receiving antenna to be stationed at a distance from about 1 foot to about 10 feet from the cart while maintaining the electronic connection with the spectrum analyzer assembly input and the processor.

13. A method for detecting a disease, the method comprising:
exposing a patient to a testing system configured to radiate an electromagnetic field based on a frequency map, the frequency map comprising one or more resonant frequencies of a virus; and
determining whether the patient carries the virus in a time of 30 seconds or less after exposing the patient to the testing system.

14. The method of claim 13, wherein one or more of:
the testing system is a portable system such as a handheld device, and
a disease condition resonate comprises a coronavirus or its specific oligonucleotides selected from the group consisting of a severe respiratory syndrome coronavirus, a virus, an RNA virus, a SARS-CoV-2, a COVID-19, a Middle East Respiratory syndrome-related coronavirus (MERS-CoV), a human coronavirus NL63 (HCoV-NL63), a human coronavirus HKU1 (HCoV-HKU1), a human coronavirus OC43 (HCoV-OC43), a human coronavirus 229E (HCoV-229E), and a combination thereof.

15. The method of claim 13, further comprising applying a series of filters in the testing system to at least partially remove background radiation to facilitate detection of the virus in an open environment.

16. A method for detecting a virus, the method comprising:
isolating resonant frequencies of the virus including a primary frequency and one or more harmonic frequencies in a shielded facility;
refining accuracy of the isolated resonant frequencies using a spectrum analyzer assembly;
developing a frequency map based on the refined resonant frequencies; and
radiating an electromagnetic field based on the frequency map for detecting the virus.

17. The method of claim 16, wherein one or more of:
the isolating of the resonant frequencies comprises a live patient methodology, and
the isolating of the resonant frequencies comprises a specific target methodology.

18. The method of claim 16, the virus comprises a coronavirus or its specific oligonucleotides selected from the group consisting of a severe respiratory syndrome coronavirus, an RNA virus, a SARS-CoV-2, a Middle East Respiratory syndrome-related coronavirus (MERS-CoV), a human coronavirus NL63 (HCoV-NL63), a human coronavirus HKU1 (HCoV-HKU1), a human coronavirus OC43 (HCoV-OC43), a human coronavirus 229E (HCoV-229E), and a combination thereof.

19. The method of claim 16, further comprising transmitting the frequency map electronically to a remote location.

20. The method of claim 16, further comprising applying one or more filters to at least partially remove background radiation to facilitate detection of the virus in an open environment.

* * * * *